(12) United States Patent
Jassell et al.

(10) Patent No.: US 9,937,311 B2
(45) Date of Patent: Apr. 10, 2018

(54) STOPPER DEVICE

(71) Applicant: DOCSINNOVENT LIMITED, London (GB)

(72) Inventors: Surinderjit Jassell, Windsor (GB); Muhammed Nasir, Luton (GB)

(73) Assignee: ASHKAL DEVELOPMENTS LIMITED (IM)

( * ) Notice: Subject to any disclaimer, the term of this patent is extended or adjusted under 35 U.S.C. 154(b) by 126 days.

(21) Appl. No.: 14/375,109

(22) PCT Filed: Jan. 28, 2013

(86) PCT No.: PCT/GB2013/050180
§ 371 (c)(1),
(2) Date: Jul. 28, 2014

(87) PCT Pub. No.: WO2013/110954
PCT Pub. Date: Aug. 1, 2013

(65) Prior Publication Data
US 2015/0000672 A1 Jan. 1, 2015

(30) Foreign Application Priority Data
Jan. 27, 2012 (GB) .................................. 1201438.7

(51) Int. Cl.
*A61M 16/04* (2006.01)
*A61D 7/00* (2006.01)

(52) U.S. Cl.
CPC .......... *A61M 16/0447* (2014.02); *A61D 7/00* (2013.01); *A61M 16/0409* (2014.02);
(Continued)

(58) Field of Classification Search
CPC .......... A61M 16/0447; A61M 16/0443; A61M 16/0493; A61M 16/0409; A61M 16/0488;
(Continued)

(56) References Cited

U.S. PATENT DOCUMENTS

| 478,582 A | 7/1892 | Ermold | 128/204.17 |
| 2,099,127 A | 11/1937 | Leech | 128/207.15 |

(Continued)

FOREIGN PATENT DOCUMENTS

| AU | B-52036/90 | 9/1990 | ............ A61M 16/04 |
| AU | B-45803/93 | 2/1994 | ............ A61M 16/04 |

(Continued)

OTHER PUBLICATIONS

U.S. Appl. No. 12/627,844, filed Nov. 30, 2009, Nasir.
(Continued)

*Primary Examiner* — (Jackie) Tan-Uyen T Ho
*Assistant Examiner* — Jonathan Paciorek
(74) *Attorney, Agent, or Firm* — Hayes-Soloway P.C.

(57) ABSTRACT

An airway device includes an airway tube having a first end surrounded by a laryngeal cuff which includes a back dorsal portion, a front face portion and a tip portion. The front face portion is shaped to form an anatomical fit over the laryngeal inlet of a patient, and to form a seal with the laryngeal inlet of the patient. The tip portion includes an annular sealing bulge which is adapted to wedge into an upper esophagus region of the patient. The annular sealing bulge improves sealing of the tip of the laryngeal cuff in the upper esophageal region of the patient. The annular sealing bulge is preferably formed from a soft polymeric or other plastics material with a Shore hardness of between 40 and 000 on the A scale, and allows for better sealing with a more variable range of upper esophageal anatomical features.

12 Claims, 27 Drawing Sheets

(52) U.S. Cl.
CPC .... *A61M 16/0443* (2014.02); *A61M 16/0488* (2013.01); *A61M 16/0493* (2014.02); *A61M 2205/0216* (2013.01); *A61M 2210/065* (2013.01); *A61M 2210/105* (2013.01); *A61M 2210/1028* (2013.01); *A61M 2210/1046* (2013.01)

(58) Field of Classification Search
CPC .. A61M 2205/0216; A61M 2210/1028; A61M 2210/105; A61M 2210/065; A61M 2210/1046; A61D 7/00
USPC ..................................... 128/207.15, 207.26
See application file for complete search history.

(56) References Cited

U.S. PATENT DOCUMENTS

| | | | |
|---|---|---|---|
| 3,443,564 A | 5/1969 | Oehmig | 128/351 |
| 3,616,799 A | 11/1971 | Sparks | 128/351 |
| 3,734,100 A | 5/1973 | Walker et al. | 128/351 |
| 3,968,800 A | 7/1976 | Vilasi | 128/343 |
| 3,995,643 A | 12/1976 | Merav | 128/351 |
| 4,509,514 A | 4/1985 | Brain | 128/207.15 |
| 4,913,139 A * | 4/1990 | Ballew | A61M 16/0488 128/200.11 |
| 4,919,126 A | 4/1990 | Baildon | 128/207.14 |
| 4,995,388 A * | 2/1991 | Brain | A61M 16/04 128/207.14 |
| 5,054,483 A | 10/1991 | Marten et al. | 128/207.14 |
| 5,174,283 A | 12/1992 | Parker | 128/200.26 |
| 5,181,505 A | 1/1993 | Lew | 128/200.26 |
| 5,241,956 A | 9/1993 | Brain | 128/207.15 |
| 5,249,571 A | 10/1993 | Brain | 128/207.14 |
| 5,259,371 A | 11/1993 | Tonrey | 128/207.15 |
| 5,282,464 A | 2/1994 | Brain | 128/207.15 |
| 5,285,778 A | 2/1994 | Mackin | 128/207.15 |
| 5,297,547 A | 3/1994 | Brain | 128/207.15 |
| 5,303,697 A | 4/1994 | Brain | 128/200.26 |
| 5,305,743 A | 4/1994 | Brain | 128/200.26 |
| 5,309,906 A | 5/1994 | LaBombard | 128/207.14 |
| 5,322,062 A | 6/1994 | Servas | 128/207.14 |
| 5,339,805 A | 8/1994 | Parker | 128/200.26 |
| 5,355,879 A | 10/1994 | Brain | 128/207.15 |
| 5,391,248 A | 2/1995 | Brain | 156/242 |
| 5,477,851 A | 12/1995 | Callaghan et al. | 28/207.15 |
| 5,584,290 A | 12/1996 | Brain | 128/207.15 |
| 5,605,149 A | 2/1997 | Wafters | 128/207.14 |
| 5,618,267 A | 4/1997 | Palestrant | 605/53 |
| 5,623,921 A | 4/1997 | Kinsinger et al. | 128/200.26 |
| 5,632,271 A | 5/1997 | Brain | 128/207.15 |
| 5,653,229 A * | 8/1997 | Greenberg | A61M 16/04 128/200.26 |
| 5,655,519 A | 8/1997 | Alfery | 128/200.26 |
| 5,682,880 A | 11/1997 | Brain | 128/207.15 |
| 5,711,293 A | 1/1998 | Brain | 128/200.24 |
| 5,791,341 A | 8/1998 | Bullard | 128/207.15 |
| 5,853,004 A | 12/1998 | Goodman | 128/207.15 |
| 5,865,176 A | 2/1999 | O'Neil | 128/207.15 |
| 5,878,745 A | 3/1999 | Brain | 128/207.15 |
| 5,881,726 A | 3/1999 | Neame | 128/207.15 |
| 5,896,858 A | 4/1999 | Brain | 128/207.15 |
| 5,915,383 A | 6/1999 | Pagan | 128/207.15 |
| 5,921,988 A | 7/1999 | Legrand | 606/87 |
| 5,937,859 A | 8/1999 | Augustine et al. | 128/207.15 |
| 5,937,860 A | 8/1999 | Cook | 28/207.15 |
| 5,964,217 A | 10/1999 | Christopher | 128/200.26 |
| 5,976,072 A | 11/1999 | Greenberg | 600/120 |
| 5,979,445 A | 11/1999 | Neame et al. | 28/207.15 |
| 5,988,167 A | 11/1999 | Kamen | 128/207.15 |
| 6,003,514 A | 12/1999 | Pagan | 128/207.15 |
| 6,055,984 A | 5/2000 | Brain | 128/207.14 |
| 6,070,581 A * | 6/2000 | Augustine | A61B 1/267 128/200.26 |
| 6,079,409 A | 6/2000 | Brain | 128/200.26 |
| D429,811 S | 8/2000 | Bermudez | D24/110.5 |
| 6,095,144 A | 8/2000 | Pagan | 128/207.15 |
| 6,152,136 A | 11/2000 | Pagan | 128/207.15 |
| 6,216,696 B1 | 4/2001 | van den Berg | 128/207.14 |
| 6,280,675 B1 | 8/2001 | Legrand | 264/262 |
| 6,311,688 B1 | 11/2001 | Augustine et al. | 128/200.26 |
| 6,318,367 B1 | 11/2001 | Mongeon | 128/207.15 |
| 6,422,239 B1 | 7/2002 | Cook | 128/207.15 |
| 6,439,232 B1 | 8/2002 | Brain | 128/207.15 |
| 6,474,332 B2 | 11/2002 | Arndt | 128/200.26 |
| 6,536,437 B1 | 3/2003 | Dragisic | 128/207.18 |
| 6,604,525 B2 | 8/2003 | Pagan | 128/207.15 |
| 6,631,720 B1 | 10/2003 | Brain | 128/207.14 |
| D482,118 S | 11/2003 | Dave et al. | D24/110 |
| 6,672,305 B2 * | 1/2004 | Parker | A61M 16/0488 128/200.26 |
| 6,679,263 B2 | 1/2004 | Luchetti et al. | 128/207.15 |
| 6,698,430 B2 | 3/2004 | Van Landuyt | 128/207.15 |
| 6,705,318 B1 | 3/2004 | Brain | 128/207.14 |
| 6,705,321 B2 | 3/2004 | Cook | 128/207.15 |
| 6,705,322 B2 | 3/2004 | Chang | 128/207.15 |
| 6,792,948 B2 | 9/2004 | Brain | 128/207.14 |
| 6,799,574 B1 | 10/2004 | Collins | 128/207.15 |
| 6,877,512 B2 | 4/2005 | Imai et al. | 128/207.15 |
| 6,918,388 B2 | 7/2005 | Brain | 128/200.26 |
| 6,918,391 B1 | 7/2005 | Moore | 128/842 |
| 6,971,382 B1 | 12/2005 | Corso | 128/200.26 |
| 7,004,169 B2 | 2/2006 | Brain | 128/207.14 |
| D518,572 S | 4/2006 | Nasir | D24/110.5 |
| D518,890 S | 4/2006 | Nasir | D24/110.5 |
| 7,040,312 B2 | 5/2006 | Alfery et al. | 128/200.26 |
| 7,040,322 B2 | 5/2006 | Fortuna | 128/207.15 |
| 7,047,973 B2 | 5/2006 | Chang | 128/207.15 |
| 7,096,868 B2 | 8/2006 | Tateo et al. | 128/207.15 |
| 7,097,802 B2 | 8/2006 | Brain | 264/255 |
| 7,134,431 B2 | 11/2006 | Brain | 128/200.26 |
| 7,140,368 B1 | 11/2006 | Collins | 128/207.14 |
| D542,675 S | 5/2007 | Luxton et al. | D9/749 |
| 7,263,998 B2 | 9/2007 | Miller | 28/207.15 |
| RE39,938 E | 12/2007 | Brain | 128/207.15 |
| 7,305,985 B2 | 12/2007 | Brain | 128/200.26 |
| 7,357,845 B2 | 4/2008 | Cook | 156/242 |
| 7,506,648 B2 | 3/2009 | Brain | 128/207.15 |
| D611,138 S | 3/2010 | Nasir | D24/110.5 |
| D615,188 S | 5/2010 | Nasir | D24/110.5 |
| D618,788 S | 6/2010 | Dubach | D24/110.5 |
| 7,762,261 B1 | 7/2010 | Fortuna | 128/207.14 |
| 7,806,119 B2 | 10/2010 | Nasir | 128/205.25 |
| 7,896,007 B2 | 3/2011 | Brain | 128/207.15 |
| 7,900,632 B2 | 3/2011 | Cook | 128/207.14 |
| 8,001,964 B2 | 8/2011 | McDonald et al. | 128/200.26 |
| D650,520 S | 12/2011 | Timmermans | D27/163 |
| 8,091,242 B2 | 1/2012 | Teys et al. | 30/324 |
| 8,215,307 B2 | 7/2012 | Nasir | 128/207.15 |
| D665,495 S | 8/2012 | Nasir | D24/110.5 |
| D693,920 S | 11/2013 | Miller | D24/110.5 |
| 9,265,905 B2 * | 2/2016 | Nasir | A61M 16/04 |
| 2001/0015207 A1 | 8/2001 | Pagan | 128/207.15 |
| 2001/0025641 A1 | 10/2001 | Doane et al. | 128/207.15 |
| 2001/0027793 A1 | 10/2001 | Tielemans | 128/848 |
| 2002/0010417 A1 | 1/2002 | Bertram | 604/96.01 |
| 2002/0010617 A1 | 1/2002 | Hamaguchi et al. | 705/10 |
| 2002/0078961 A1 | 6/2002 | Collins | 128/207.15 |
| 2002/0103472 A1 | 8/2002 | Kramer | 604/507 |
| 2002/0108610 A1 | 8/2002 | Christopher | 128/200.26 |
| 2002/0112728 A1 | 8/2002 | Landuyt | 128/207.15 |
| 2002/0170556 A1 | 11/2002 | Gaitini | 128/200.14 |
| 2003/0037790 A1 | 2/2003 | Brain | 128/207.14 |
| 2003/0066532 A1 | 4/2003 | Gobel | 128/207.15 |
| 2003/0101998 A1 | 6/2003 | Zocca et al. | 128/207.15 |
| 2003/0136413 A1 | 7/2003 | Brain et al. | 128/207.15 |
| 2003/0172925 A1 | 9/2003 | Zocca et al. | 128/202.22 |
| 2003/0172933 A1 | 9/2003 | Nimmo | 128/207.14 |
| 2004/0020488 A1 | 2/2004 | Kniewasser | 128/204.18 |
| 2004/0020491 A1 | 2/2004 | Fortuna | 128/207.15 |
| 2004/0060564 A1 | 4/2004 | Brain | A61M 16/00 |
| 2005/0016529 A1 | 1/2005 | Cook | 128/200.24 |
| 2005/0051173 A1 | 3/2005 | Brain | 128/207.14 |
| 2005/0051175 A1 | 3/2005 | Brain | 128/207.14 |
| 2005/0066975 A1 | 3/2005 | Brain | 128/207.15 |

(56) References Cited

U.S. PATENT DOCUMENTS

| | | | |
|---|---|---|---|
| 2005/0081861 A1 | 4/2005 | Nashir | 128/207.14 |
| 2005/0103345 A1 | 5/2005 | Brain | 128/207.15 |
| 2005/0104255 A1 | 5/2005 | Mejlhede et al. | 264/328.1 |
| 2005/0274383 A1 | 12/2005 | Brain | 128/207.15 |
| 2006/0081245 A1 | 4/2006 | Gould | 128/200.26 |
| 2006/0207601 A1 | 9/2006 | Nasir | 128/207.14 |
| 2007/0137651 A1 | 6/2007 | Glassenberg et al. | 128/207.15 |
| 2008/0142017 A1 | 6/2008 | Brain | 128/207.15 |
| 2008/0236590 A1 | 10/2008 | Reissmann | 128/207.14 |
| 2008/0308109 A1 | 12/2008 | Brain | 128/207.14 |
| 2009/0090356 A1 | 4/2009 | Cook | 128/200.26 |
| 2010/0059061 A1 | 3/2010 | Brain | 128/207.14 |
| 2010/0089393 A1 | 4/2010 | Brain | 128/203.12 |
| 2010/0126512 A1* | 5/2010 | Nasir | A61M 16/04 128/207.14 |
| 2010/0147309 A1 | 6/2010 | Cuevas et al. | 128/207.14 |
| 2010/0242957 A1 | 9/2010 | Fortuna | 128/202.22 |
| 2011/0226256 A1 | 9/2011 | Dubach | A61M 16/06 |
| 2011/0265799 A1 | 11/2011 | Lisogurski | 128/207.15 |
| 2011/0277772 A1 | 11/2011 | Nasir | 128/207.15 |
| 2012/0024292 A1 | 2/2012 | Sandmore et al. | 128/207.14 |
| 2013/0092172 A1 | 4/2013 | Nasir | 128/207.15 |
| 2013/0247917 A1 | 9/2013 | Brain | 128/207.15 |
| 2013/0324798 A1 | 12/2013 | Molnar et al. | 600/120 |
| 2015/0000672 A1 | 1/2015 | Jassell | 128/207.15 |

FOREIGN PATENT DOCUMENTS

| | | | | |
|---|---|---|---|---|
| AU | 200076743 | 5/2001 | | A61M 16/04 |
| CA | 1 324 551 | 11/1993 | | A61M 16/04 |
| CA | 2 191 749 | 12/1995 | | A61M 16/01 |
| CA | 2 346 248 | 4/2000 | | A61M 16/04 |
| CN | 1 166 138 | 11/1997 | | A61M 16/00 |
| CN | 1 236 326 | 11/1999 | | A61M 16/04 |
| CN | 1 351 509 | 5/2002 | | A61M 16/04 |
| DE | 42 33 933 | 4/1993 | | H02N 2/00 |
| DE | 43 30 032 | 4/1994 | | H02N 2/00 |
| DE | 195 00 550 | 7/1996 | | A61M 16/04 |
| DE | 299 02 267 | 7/1999 | | A61M 16/06 |
| DE | 201 00 176 | 5/2001 | | A61M 16/01 |
| DE | 202 06 692 | 8/2002 | | A61M 16/00 |
| EM | 000067210-0001 | 8/2003 | | |
| EM | 000067210-0002 | 8/2003 | | |
| EM | 000197124-0001 | 6/2004 | | |
| EM | 000197124-0002 | 6/2004 | | |
| EM | 000197124-0003 | 6/2004 | | |
| EM | 000197124-0004 | 6/2004 | | |
| EM | 000197124-0005 | 6/2004 | | |
| EM | 000197124-0006 | 6/2004 | | |
| EM | 000180757-0001 | 7/2004 | | |
| EM | 000482195-0001 | 2/2006 | | |
| EM | 000482195-0002 | 2/2006 | | |
| EP | 0 277 797 | 8/1988 | | A61M 16/04 |
| EP | 0 389 272 | 9/1990 | | A61M 16/04 |
| EP | 0 448 878 | 10/1991 | | A61M 16/04 |
| EP | 0 586 717 | 3/1994 | | A61M 16/04 |
| EP | 0 794 807 | 9/1997 | | A61M 16/00 |
| EP | 0 834 331 | 8/1998 | | A61M 16/04 |
| EP | 0 857 492 | 8/1998 | | A61M 16/04 |
| EP | 0 875 260 | 11/1998 | | A61M 16/04 |
| EP | 0 884 061 | 12/1998 | | A61M 16/04 |
| EP | 0 911 049 | 4/1999 | | A61M 16/04 |
| EP | 0 935 971 | 8/1999 | | A61M 16/04 |
| EP | 1 125 595 | 8/2001 | | A61M 16/04 |
| EP | 1504870 | 2/2005 | | |
| EP | 1 579 885 | 9/2005 | | A61M 16/04 |
| EP | 1220701 | 3/2007 | | A61M 16/04 |
| EP | 1169077 | 12/2007 | | A61M 16/04 |
| EP | 1 875 937 | 1/2008 | | A61M 16/04 |
| ES | 1 046 206 | 12/2000 | | A61M 25/00 |
| FR | 2 094 264 | 1/1972 | | C07C 31/00 |
| FR | 2 690 018 | 10/1993 | | H02N 2/00 |
| FR | 2 760 186 | 9/1998 | | A61F 2/30 |
| FR | 2 807 307 | 10/2001 | | A47J 37/06 |
| FR | 2 827 482 | 1/2003 | | A24B 1/10 |
| FR | 2 851 107 | 8/2004 | | H04M 11/06 |
| GB | 1 402 255 | 8/1975 | | A61M 25/00 |
| GB | 2 113 348 | 8/1983 | | B06B 1/16 |
| GB | 2 128 561 | 5/1984 | | B60R 19/54 |
| GB | 2 168 256 | 6/1986 | | A61M 16/04 |
| GB | 2 249 959 | 5/1992 | | A61M 16/04 |
| GB | 2 267 034 | 11/1993 | | A61M 25/02 |
| GB | 2 285 765 | 7/1995 | | A61M 16/04 |
| GB | 2 317 342 | 3/1998 | | A61M 16/04 |
| GB | 2 319 182 | 5/1998 | | A61M 16/04 |
| GB | 2 323 292 | 9/1998 | | A61M 16/04 |
| GB | 2 326 009 | 12/1998 | | A61M 16/04 |
| GB | 2 330 312 | 4/1999 | | A61M 16/04 |
| GB | 2 337 020 | 11/1999 | | B29D 31/00 |
| GB | 2 359 996 | 9/2001 | | A61M 16/04 |
| GB | 2 364 644 | 2/2002 | | A61M 16/04 |
| GB | 2 373 188 | 9/2002 | | A61M 16/04 |
| GB | 2 393 399 | 3/2004 | | A61M 16/04 |
| GB | 2 404 863 | 2/2005 | | A61M 16/04 |
| GB | 2 413 963 | 11/2005 | | A61M 16/04 |
| GB | 2438799 | 12/2007 | | A61M 16/04 |
| GB | 2 465 453 | 5/2010 | | A61M 16/04 |
| GB | 2479823 | 10/2011 | | A61M 16/12 |
| GB | 2481538 | 12/2011 | | A61M 16/04 |
| IE | 922073 | 12/1993 | | A61M 16/00 |
| IT | 1224077 | 9/1990 | | |
| JP | 3-236858 | 10/1991 | | A61M 16/04 |
| JP | 6/277286 | 10/1994 | | A61M 16/04 |
| JP | 2706567 | 1/1998 | | A61B 1/00 |
| JP | 2007-509154 | 4/2007 | | A61K 31/4409 |
| TW | 224047 | 11/2004 | | B29C 45/76 |
| WO | WO91/12844 | 9/1991 | | A61M 16/04 |
| WO | WO 94/17848 | 8/1994 | | A61M 16/04 |
| WO | WO 95/09665 | 4/1995 | | A61M 16/04 |
| WO | WO 97/12640 | 4/1997 | | A61M 16/00 |
| WO | WO 98/06276 | 2/1998 | | A23L 1/30 |
| WO | WO 98/24498 | 6/1998 | | A61M 16/04 |
| WO | WO 98/50096 | 11/1998 | | A61M 16/00 |
| WO | WO 99/24101 | 5/1999 | | A61M 16/00 |
| WO | WO 99/44665 | 9/1999 | | A61M 16/04 |
| WO | WO 00/09189 | 2/2000 | | A61M 16/04 |
| WO | WO 00/30706 | 6/2000 | | A61M 16/04 |
| WO | WO 00/61213 | 10/2000 | | A61M 16/04 |
| WO | WO112844 | 2/2001 | | C12Q 1/34 |
| WO | WO 01/13980 | 3/2001 | | A61M 16/04 |
| WO | WO2011131974 | 10/2001 | | A61M 16/04 |
| WO | WO 0197890 | 12/2001 | | A61M 16/00 |
| WO | WO 02/32490 | 4/2002 | | A61M 16/04 |
| WO | WO 03/020340 | 3/2003 | | A61M 16/04 |
| WO | WO 03018094 | 3/2003 | | A61M 16/04 |
| WO | WO 2004/016308 | 2/2004 | | A61M 16/04 |
| WO | WO2004/089453 | 10/2004 | | |
| WO | WO 2005/016427 | 2/2005 | | A61M 16/04 |
| WO | WO 2005/041864 | 5/2005 | | A61K 31/415 |
| WO | WO2006/125986 | 11/2006 | | A61M 16/04 |
| WO | WO 2009/129081 | 10/2009 | | A61M 16/04 |
| WO | WO2009142821 | 11/2009 | | A61B 1/31 |
| WO | WO 2011161473 | 12/2011 | | A61M 16/04 |
| WO | WO2014058840 | 4/2014 | | A61M 16/00 |
| WO | WO2014159522 | 10/2014 | | A61M 16/04 |

OTHER PUBLICATIONS

U.S. Appl. No. 29/428,284, filed Jul. 27, 2012, Nasir et al.
U.S. Appl. No. 13/805,956, filed Dec. 20, 2012, Nasir et al.
U.S. Appl. No. 29/475,489, filed Dec. 3, 2013, Miller et al.
U.S. Appl. No. 14/315,141, filed Jun. 25, 2014, Nasir.
U.S. Appl. No. 14/315,149, filed Jun. 25, 2014, Nasir.
Office Action issued in related U.S. Appl. No. 29/428,284, dated Oct. 6, 2014 (66 pgs).
Office Action issued in related U.S. Appl. No. 12/627,844, dated Oct. 23, 2014 (38 pgs).
Office Action issued in related U.S. Appl. No. 29/475,489, dated Dec. 4, 2014 (13 pgs).
Great Britain Combined Search and Examination Report issued in application No. GB1322330.0, dated May 20, 2015 (8 pgs).

(56) References Cited

OTHER PUBLICATIONS

Great Britain Combined Search and Examination Report issued in application No. GB1322328.4, dated Feb. 26, 2015 (8 pgs).
International Preliminary Report on Patentability issued in application No. PCT/GB2014/053744, dated Jun. 21, 2016 (9 pgs).
International Preliminary Report on Patentability issued in application No. PCT/GB2014/053745, dated Jun. 21, 2016 (9 pgs).
International Search Report and Written Opinion issued in application No. PCT/GB2014/053745, dated Mar. 11, 2015 (14 pgs).
International Search Report and Written Opinion issued in application No. PCT/GB2014/053744, dated Jul. 14, 2015 (15 pgs).
Office Action issued in U.S. Appl. No. 12/627,844, dated Sep. 17, 2015 (26 pgs).
Office Action issued in U.S. Appl. No. 29/428,284, dated Mar. 19, 2015 (6 pgs).
Notice of Allowance issued in U.S. Appl. No. 14/315,141, dated. Nov. 13, 2015 (36 pgs).
Office Action issued in U.S. Appl. No. 29/428,284, dated Nov. 10, 2015 (5 pgs).
Office Action issued in U.S. Appl. No. 29/512,931, dated Nov. 23, 2015 (20 pgs).
Office Action issued in U.S. Appl. No. 29/512,932, dated Nov. 19, 2015 (19 pgs).
Notice of Allowance issued in U.S. Appl. No. 13/805,956, dated Dec. 21, 2015 (26 pgs).
U.S. Appl. No. 29/512,931, filed Dec. 23, 2014, Nasir et al.
U.S. Appl. No. 29/512,932, filed Dec. 23, 2014, Nasir et al.
Notice of Allowance issued in U.S. Appl. No. 29/428,284, dated Mar. 8, 2016 (17 pgs).
Notice of Allowance issued in U.S. Appl. No. 14/315,149, dated Mar. 11, 2016 (42 pgs).
Office Action issued in U.S. Appl. No. 29/512,931, dated Mar. 8, 2016 (8 pgs).
Office Action issued in U.S. Appl. No. 29/512,932, dated Mar. 8, 2016 (8 pgs).
Office Action issued in U.S. Appl. No. 12/627,844, dated May 5, 2016 (33 pgs).
U.S. Appl. No. 14/215,149, filed Jun. 25, 2014, Nasir.
Notice of Allowance issued in U.S. Appl. No. 14/315,149, dated Aug. 30, 2016 (16 pgs).
U.S. Appl. No. 13/130,555, filed May 20, 2011, Nasir.
U.S. Appl. No. 29/416,561, filed Mar. 23, 2012, Miller et al.
"The Development of the Laryngeal Mask-a Brief History of the Invention, Early Clinical Studies and Experimental Work from Which the Laryngeal Mask Evolved" A.I.J. Brain, European Journal of Anesthesiology, 1991, Supplement 4, pp. 5-17.
PCT International Search Report, PCT Application Serial No. PCT/GB2008/050880, dated Jan. 14, 2009 (20 pgs).
Office Action issued in U.S. Appl. No. 29/353,658 dated Aug. 19, 2011 (10 pgs).
International Search Report and Written Opinion issued in Applicant's corresponding UK Patent Application Serial No. GB0817776.8.
International Search Report and Written Opinion issued in corresponding application No. PCT/GB2011/051203, dated Jul. 12, 2011 (14 pgs).
UK Search Report issued in corresponding application No. GB1110775.2, dated Oct. 18, 2011. (8 pgs).
U.S. Office Action dated Feb. 14, 2013, issued in U.S. Appl. No. 29/407,461 (21 pgs).
International Search Report and Written Opinion issued in corresponding application No. PCT/GB2011/051203, dated Dec. 7, 2011 (15 pgs).
Combined Search and Examination Report issued in corresponding application No. GB1110775.2, dated Oct. 18, 2011 (8 pgs).
Combined Search and Examination Report issued in corresponding application No. GB0718849.3, dated Oct. 29, 2007 (4 pgs).
Combined Search and Examination Report issued in corresponding application No. GB0502519.2, dated Sep. 13, 2005 (6 pgs).

Extended European Search Report and Written Opinion issued in corresponding EPO application No. 07019251.3, dated Feb. 1, 2008 (8 pgs).
First Office Action issued in corresponding Chinese application No. 200480023382.4, dated Aug. 22, 2008 (15 pgs).
International Search Report and Written Opinion issued in corresponding PCT application No. PCT/GB2009/051574 dated Jun. 7, 2010 (28 pgs).
Combined Search and Examination Report issued in corresponding application No. GB1019839.8, dated. Dec. 1, 2010 (2 pgs).
Combined Search and Examination Report issued in corresponding application No. GB 0418050.1, dated Nov. 29, 2004 (7 pgs).
Examination Report issued in corresponding application No. 09 756 353.0-1257, dated Aug. 17, 2012 (5 pgs).
Further examination as result of telephone conversation with examiner issued in corresponding EPO application No. 03 787 902.0 (1 pg).
Letter from IP Australia regarding third party application for re-examination dated Sep. 21, 2011 involving corresponding application No. 2008207412 (2 pgs).
Invitation to Pay Additional Fees with International Search Report issued in corresponding application No. PCT/GB2004/003481, dated Nov. 12, 2004 (8 pgs).
Notice for Reasons for Rejection issued in corresponding Japanese application No. 2006/523053, dated Nov. 8, 2010, with English translation (4 pgs).
International Search Authority issued in corresponding PCT application PCT/GB03/03577 dated, Dec. 9, 2003 (5 pgs).
International Search Report issued in corresponding PCT application PCT/GB03/03577 dated Aug. 14, 2003 (9 pgs).
Japanese Office Action (no translation) issued in related application No. 2012-38633, dated Apr. 23, 2013 (2 pgs).
Office Action issued in related U.S. Appl. No. 13/403,806, dated Apr. 25, 2013 (6 pgs).
Notice of Allowance issued in related U.S. Appl. No. 29/407,461, dated Jun. 12, 2013 (26 pgs).
Notice of Allowance issued in related U.S. Appl. No. 29/449,900, dated Jul. 24, 2013 (11 pgs).
Office Action issued in related U.S. Appl. No. 13/403,806, dated Aug. 15, 2013 (45 pgs).
Office Action issued in related U.S. Appl. No. 12/627,844, dated Feb. 28, 2014 (22 pgs).
Notice of Allowance issued in related U.S. Appl. No. 13/403,806, dated Mar. 12, 2014 (16 pgs).
Notice of Allowance issued in related U.S. Appl. No. 29/416,561, dated May 9, 2014 (7 pgs).
Office Action issued in related U.S. Appl. No. 13/130,555, dated Jun. 20, 2014 (36 pgs).
Office Action issued in related U.S. Appl. No. 29/475,489, dated Jun. 20, 2014 (25 pgs).
International Search Report and Written Opinion issued in related application No. PCT/GB2013/050180, dated May 7, 2013 (13 pages).
Combined Search and Examination Report issued in related application No. GB1301478,2, dated May 23, 2013 (5 pgs).
Office Action issued in U.S. Appl. No. 12/627,844, dated Jan. 27, 2017 (28 pgs).
U.S. Appl. No. 10/983,199, filed Nov. 5, 2004.
U.S. Appl. No. 10/568,362, filed Feb. 14, 2006.
U.S. Appl. No. 12/627,844, filed Nov. 30, 2009.
U.S. Appl. No. 29/353,658, filed Jan. 12, 2010.
U.S. Appl. No. 12/680,731, filed Mar. 29, 2010.
U.S. Appl. No. 12/859,169, filed Aug. 18, 2010.
U.S. Appl. No. 13/130,555, filed May 20, 2011.
U.S. Appl. No. 29/402,009, filed Sep. 19, 2011.
U.S. Appl. No. 29/407,461, filed Nov. 29, 2011.
U.S. Appl. No. 13/403,806, filed Feb. 23, 2012.
U.S. Appl. No. 29/416,561, filed Mar. 23, 2012.
U.S. Appl. No. 29/428,284, filed Jul. 27, 2012.
U.S. Appl. No. 13/805,956, filed Dec. 20, 2012.
U.S. Appl. No. 29/449,900, filed Mar. 15, 2013.
U.S. Appl. No. 29/475,489, filed Dec. 3, 2013.
U.S. Appl. No. 14/315,141, filed Jun. 25, 2014.

(56) References Cited

OTHER PUBLICATIONS

U.S. Appl. No. 14/315,149, filed Jun. 25, 2014.
U.S. Appl. No. 29/512,931, filed Dec. 23, 2014.
U.S. Appl. No. 29/512,932, filed Dec. 23, 2014.
U.S. Appl. No. 12/627,844, filed Nov. 30,2009, Nasir.
U.S. Appl. No. 29/548,655, filed Dec. 15, 2015, Miller et al.
U.S. Appl. No. 15/106,239, filed Jun. 17, 2016, Nasir et al.
U.S. Appl. No. 15/106,243, filed Jun. 17, 2016, Nasir et al.
European Patent Office Examination Report Issued in Corresponding Application No. 14824070.8, dated Apr. 24, 2017 (9 Pages).
Great Britain Combined Search and Examination Report Issued in Corresponding Application No. GB1621321.7, dated May 4, 2017 (5 Pages).
Great Britain Examination Report Issued in Corresponding Application No. GB1322330.0 dated Mar. 8, 2016,(3 Pages).

\* cited by examiner

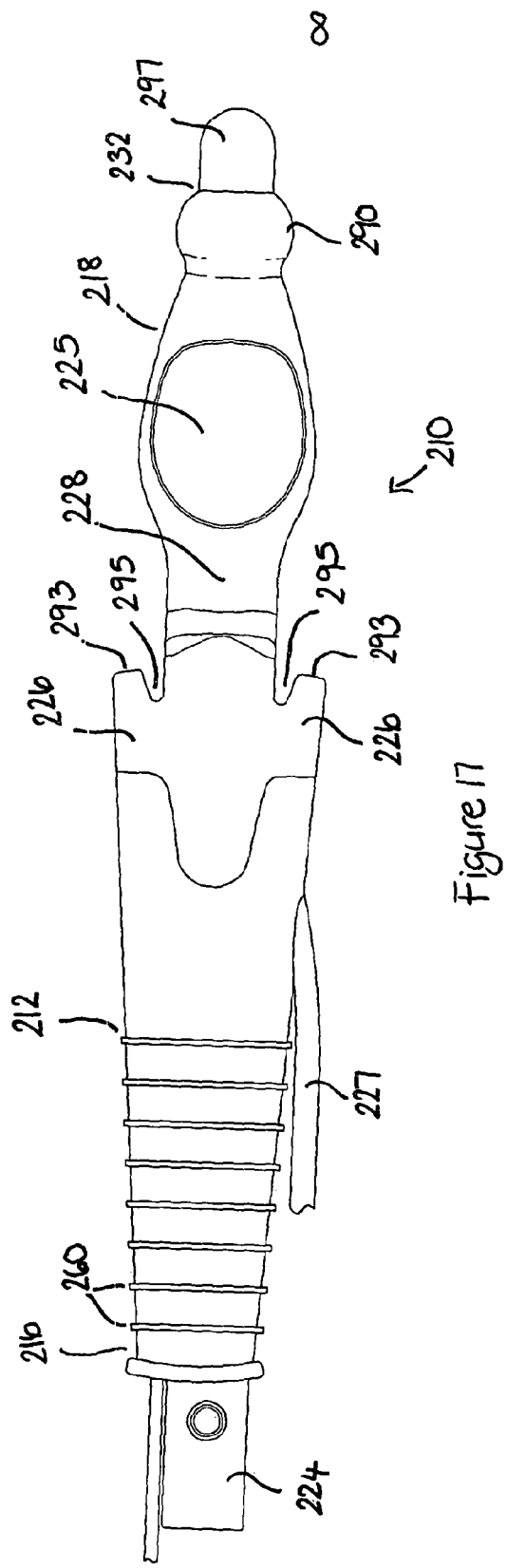
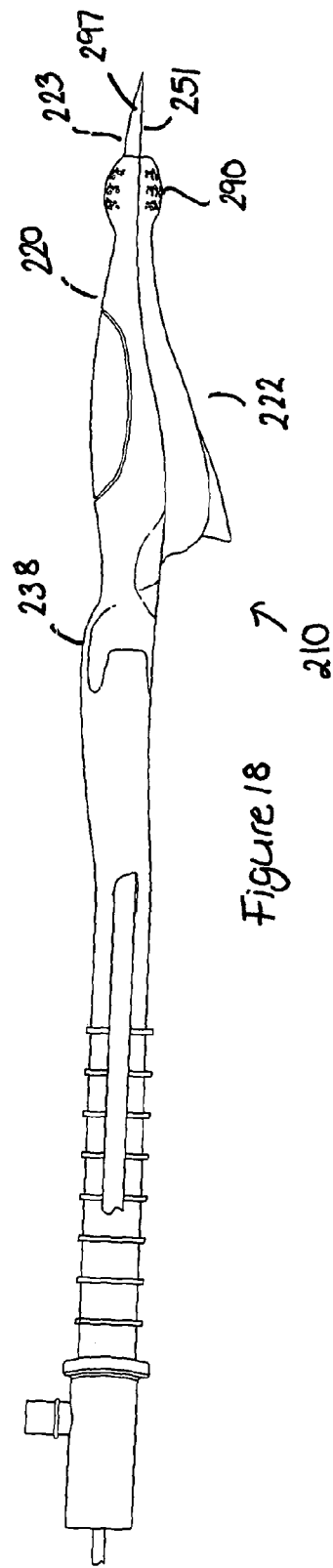
Figure 17
Figure 18

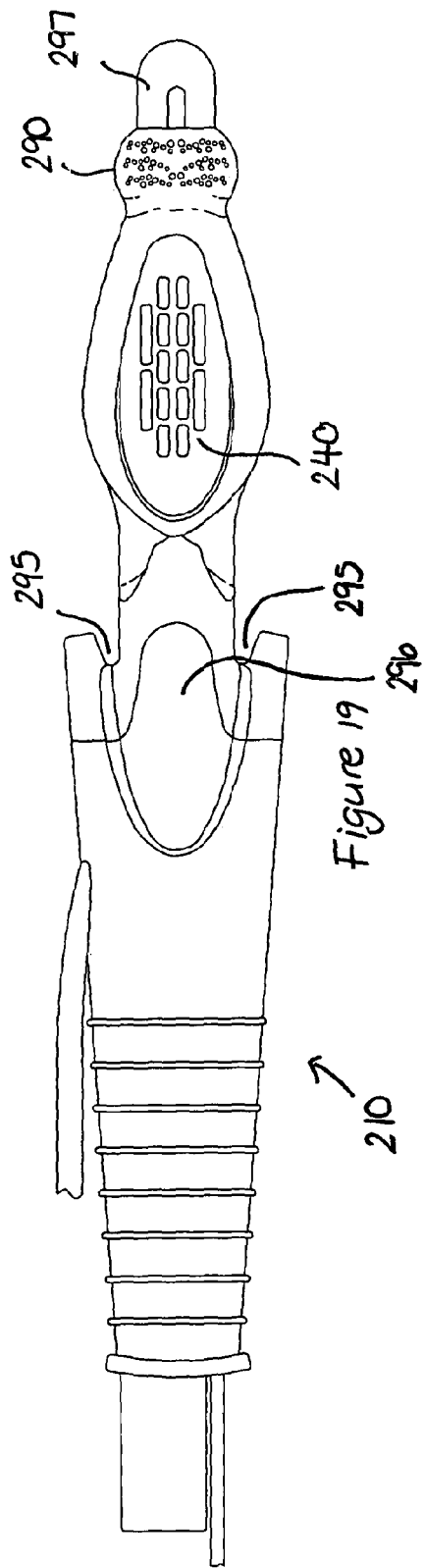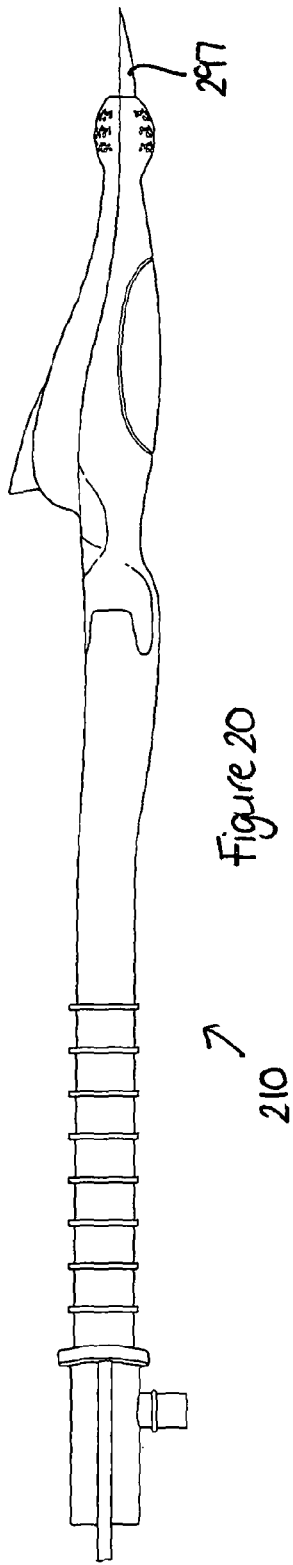

410

410

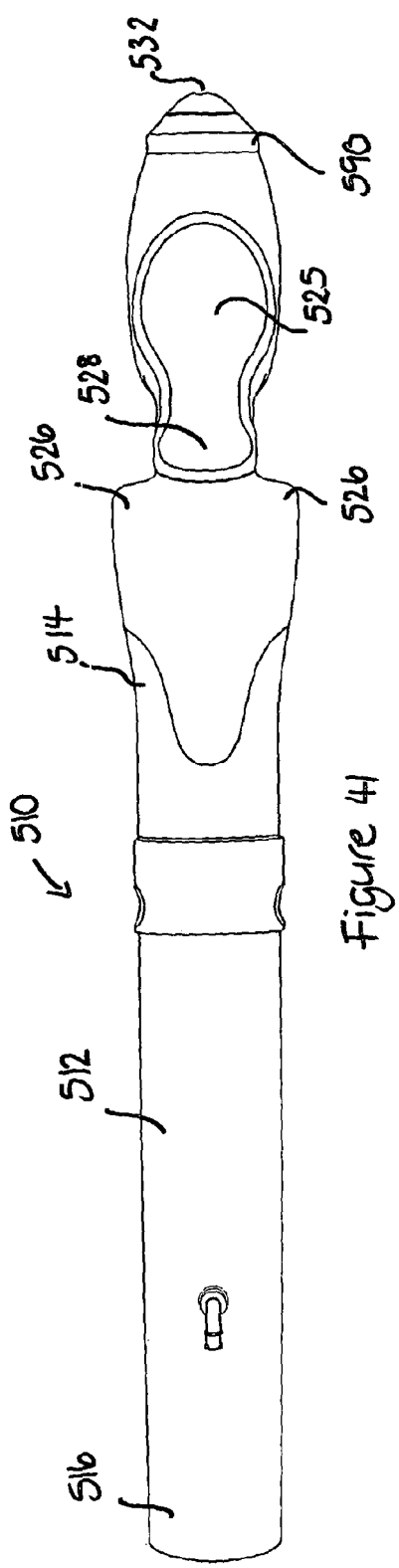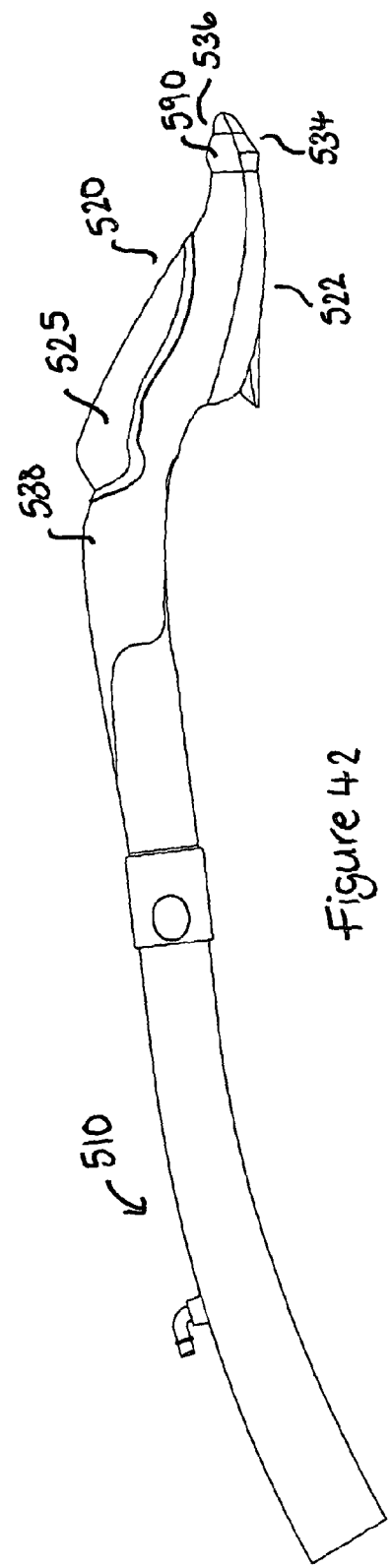
Figure 41
Figure 42

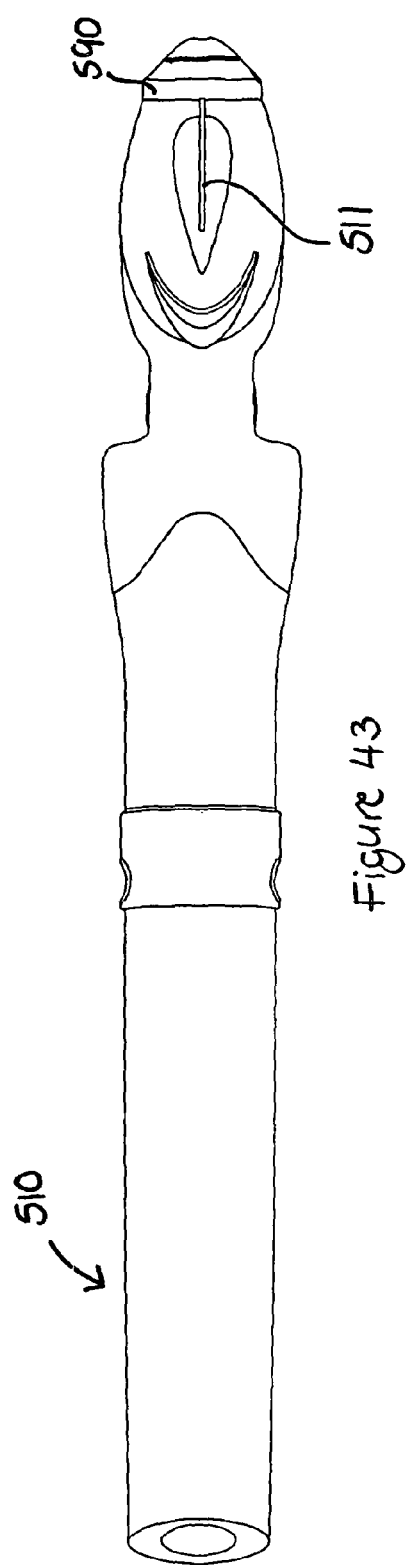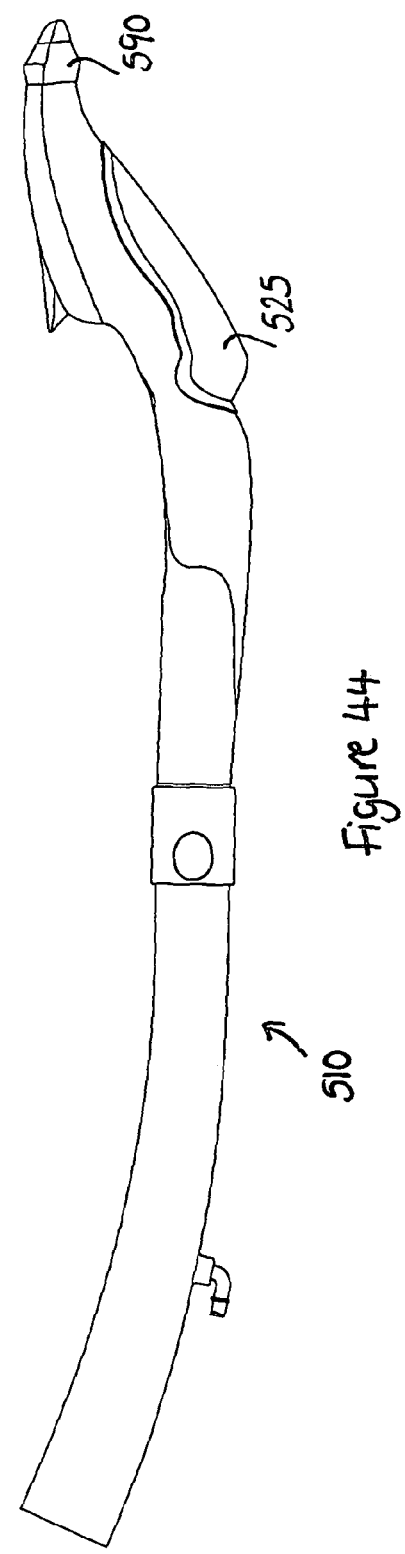
Figure 43
Figure 44

STOPPER DEVICE

The present invention relates to medical devices, namely safety airway devices. It is applicable to supraglottic devices including pharyngeal, laryngeal, and tracheal and endobroncheal airway devices and to their methods of manufacture. The present invention is also applicable to other type of devices which also involve the administration of oxygen and/or anaesthetic gases to a human or animal patient through spontaneous breathing, assisted ventilation or Intermittent Positive Pressure Ventilation (IPPV) during a surgical procedure or resuscitation.

Various airway devices are known and are currently used in spontaneous breathing or IPPV to anaesthetise patients, or for resuscitation applications. The main focus of developments in such devices has heavily leaned towards ensuring the best shape and material combination to make such devices easy to insert and to improve sealing pressures once the device is in situ within the patient. This has been the case for both supraglottic devices which seal within the larynx and endotracheal tubes which seal within the trachea.

In particular in the case of supraglottic devices, the requirement for clinical knowledge and experience is invaluable in the decision-making process of choosing the correctly sized device for a given set of patient parameters. However, such decisions can still be very subjective and are arbitrarily related to the weight of the given patient, and will therefore be variable depending on the particular experience or preferences of individual clinicians. This increases the chance of selecting and using a device of the incorrect size for the given patient. Selecting an incorrectly sized device will lead to undesirable consequences, for example if a device that is too small for the patient is chosen this is likely to result in an over-insertion of the device beyond the larynx and deep into the trachea in the case of laryngeal airway devices, which can potentially result in traumatising and/or damaging the trachea, oesophagus, vocal chords and upper oesophagus in both human and animal patients.

The issues and consequences of incorrect device selection are particularly relevant in paediatric use. In paediatrics the stage of anatomical development is in a state of constant flux, with various rates of change from individual to individual, until adulthood is reached. When adulthood is reached the shapes of the internal anatomical structures become more stable and thus provide a more reliable environment for correct device size selection and use. Therefore, in paediatrics the risk of incorrect device size selection, which may result in over insertion or lack of optimal sealing forces of a device in the patient is much greater in paediatrics than in adults. This matter is highly exacerbated within veterinary anaesthesia situations as the anatomical parameters can vary significantly not only between species but also within a species type, such as in the case of dogs.

In addition to the problem of over-insertion of such supraglottic devices, another problem which can arise is accidental rotation of the device after insertion. This type of incident could result in the device being displaced from the correct sealing position within the human or animal patient. Some attempts have been made in the prior art to produce devices which do not readily succumb to rotation after insertion. This has been done by either widening the surface area of the device that is in contact with the top of the tongue or through the use of external fixation systems. However, such attempts have not been wholly successful in solving the rotation problem. In the case of external fixation this requires an additional effort on behalf of the clinician to secure the device and therefore unfortunately this is not always undertaken.

Yet another problem which still exists in present supraglottic devices, and in particular in airway type devices, is the possibility of the epiglottis of the human or animal patient down folding and occluding the airway within the device, thus blocking off the gas flow to and from the patient. The problem associated with down folding epiglottis is most applicable to paediatric and animal patients who have a large range in both the flexibility and size of the epiglottis.

According to a first aspect of the present invention there is provided an airway device for human or animal use, the device includes an airway tube having a first end and a second end, the first end of the airway tube is surrounded by a laryngeal cuff, the laryngeal cuff includes a back dorsal portion and a front face portion, the front face portion of the laryngeal cuff is shaped to form an anatomical fit over the laryngeal inlet of a human or animal patient, and to form a seal with the laryngeal inlet of the patient, wherein the tip portion includes an annular sealing bulge. The annular sealing bulge is adapted to wedge into upper oesophagus region of the human or animal patient. The annular sealing bulge is provided for improved sealing of the tip of the laryngeal cuff in the upper oesophageal region of the human or animal patient. The annular sealing bulge is preferably formed from a soft polymeric or other plastics material with a Shore hardness of between 40 and 000 on the A scale. The annular sealing bulge allows for better sealing with a more variable range of upper oesophageal anatomical features.

In one alternative the annular sealing bulge is larger on the front face portion of the tip than on the dorsal portion of the tip. The unsymmetrical nature of the annular sealing bulge means that should the human or animal patient regurgitate or vomit whilst the airway device is in situ in the human or animal patient the regurgitate or vomit, if not completely stopped by the annular sealing bulge, is more likely to take the path of least resistance i.e. via the dorsal portion of the tip and the airway device rather than the front face portion of the tip and thus the airway device. This is safer for the human or animal patient as this means that it is less likely for the regurgitate or vomit to enter into the airway of the human or animal patient.

In a further alternative, the annular sealing bulge on the front face portion of the tip may be provided with a inner core formed from a rigid material covered or coated with a soft polymeric or other plastics material with a Shore hardness of between 40 and 000 on the A scale.

Preferably the annular sealing bulge is provided with a contoured surface, the contoured surface reduces the surface areas of the annular sealing bulge that is in contact with the upper oesophageal features of the patient when in situ in the patient to reduce trauma resulting from contact between the bulge and such features whilst still creating a good feel therewith.

In the alternative the contoured surface is a dimpled surface, in another alternative the contoured surface is a pimpled surface, in another alternative the contoured surface is provided with a series of ridges, indentations, valleys and/or protrusions, in order to minimise contact surface area whilst maximising the effectiveness of the feel.

The invention will now be described, by way of example only, with reference the accompanying drawings in which:

FIG. 17 is a top view of an airway device according to a third embodiment of the present invention;

FIG. 18 is a right side view of an airway device according to a third embodiment of the present invention;

FIG. 19 is a bottom view of an airway device according to a third embodiment of the present invention;

FIG. 20 is a left side view of an airway device according to a third embodiment of the present invention;

Figure 1:
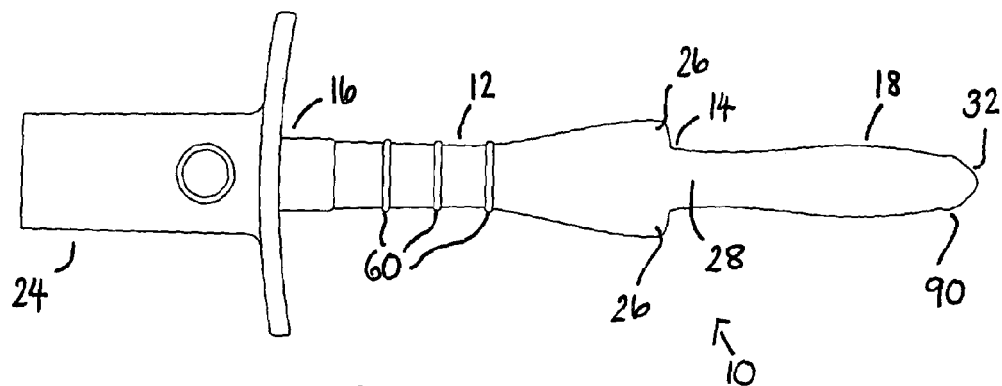
FIG. 1 is a top view of an airway device according to a first embodiment of the present invention.
Figure 2:
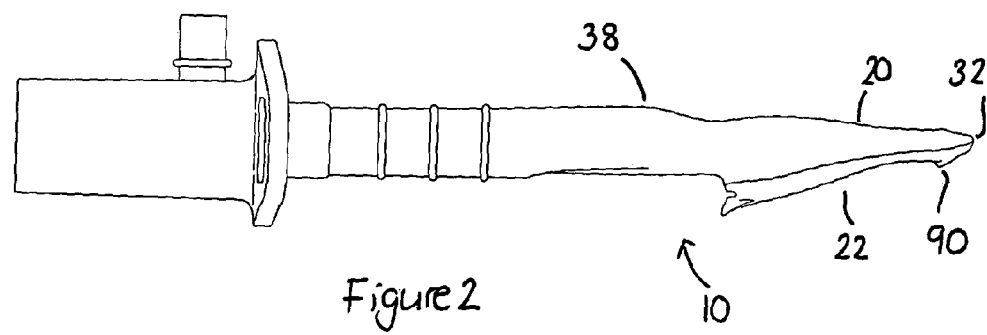
FIG. 2 is a right side view of an airway device according to a first embodiment of the present invention.
Figure 3:
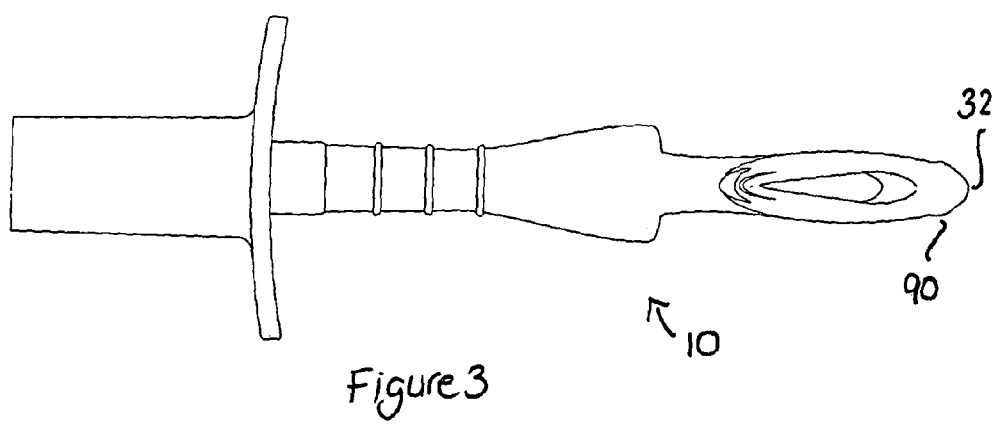
FIG. 3 is a bottom view of an airway device according to a first embodiment of the present invention.
Figure 4:
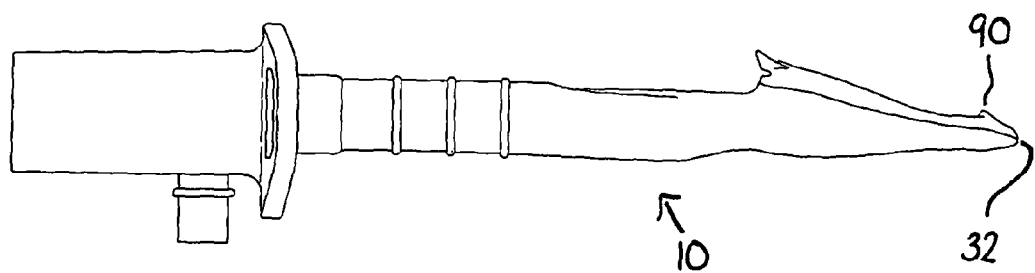
FIG. 4 is a left side view of an airway device according to a first embodiment of the present invention.
Figure 5:
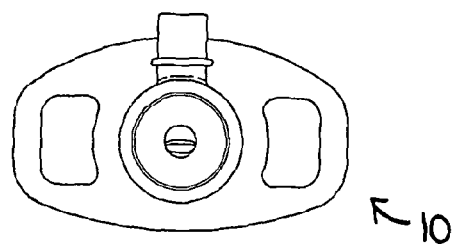
FIG. 5 is a rear view of an airway device according to a first embodiment of the present invention.
Figure 6:
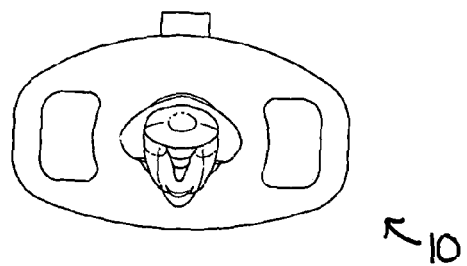
FIG. 6 is a front view of an airway device according to a first embodiment of the present invention.
Figure 7:
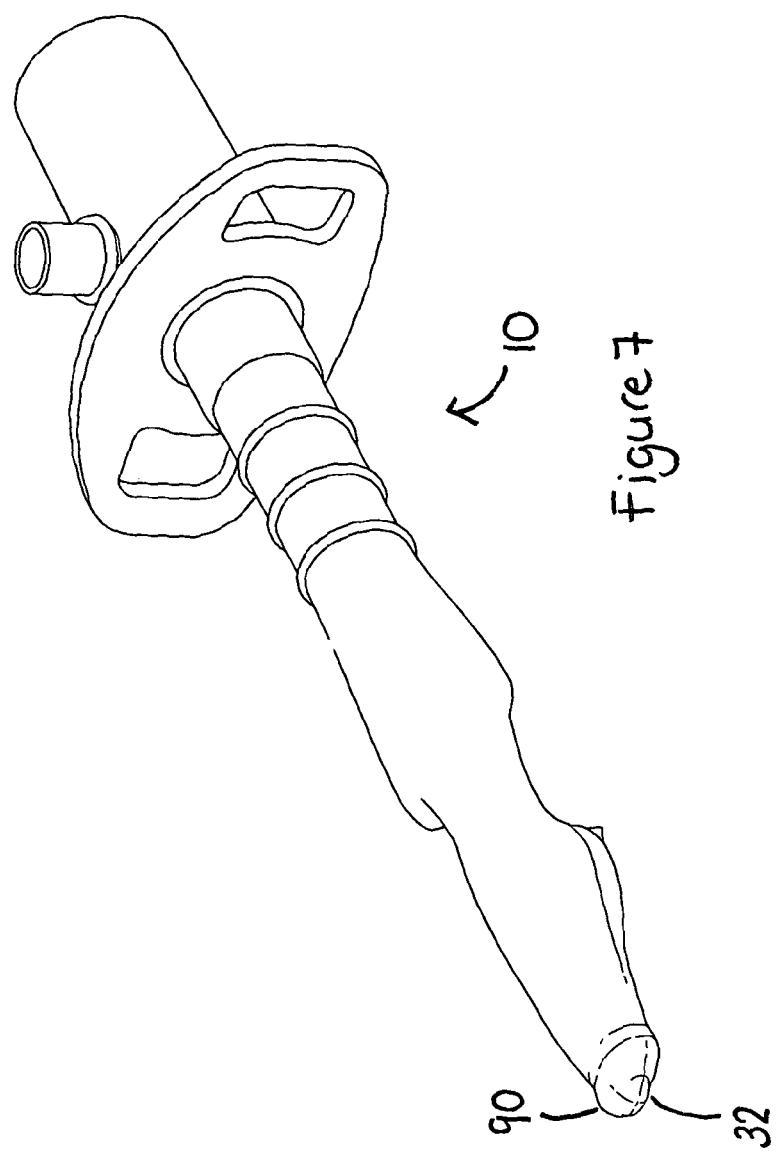
FIG. 7 is a top perspective view of an airway device according to a first embodiment of the present invention.
Figure 8:
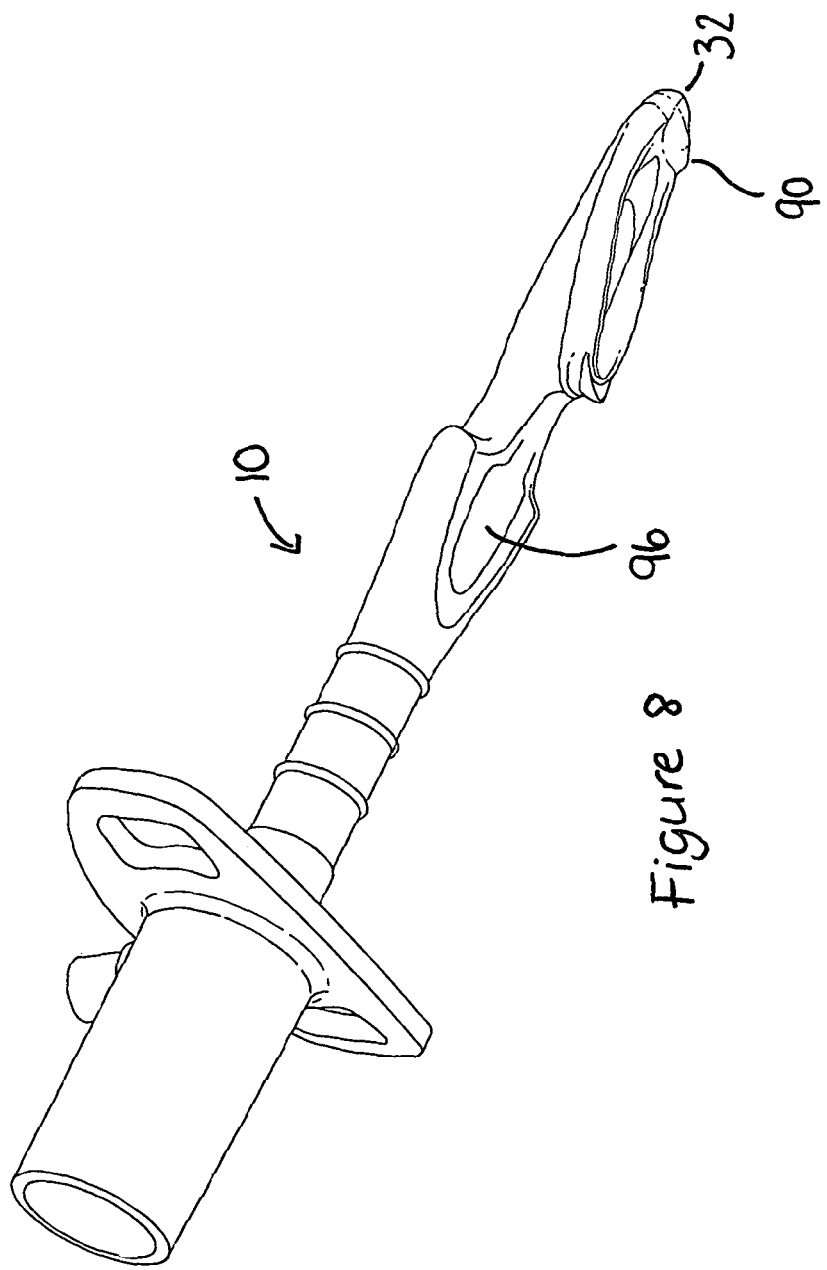
FIG. 8 is a bottom perspective view of an airway device according to a first embodiment of the present invention.

FIGS. 1 to 8 illustrate a first embodiment of an airway device 10 according to the present invention. The airway device 10 has an airway tube 12 with a first end 14 and a second end 16. The first end 14 of the airway tube 12 is surrounded by a laryngeal cuff 18. The laryngeal cuff 18 has a back dorsal portion 20 and a front face portion 22. The front face portion 22 is shaped to form an anatomical fit over the laryngeal inlet of a human or animal patient, and to form a seal with the laryngeal inlet of the patient. The second end 16 of the airway tube is fitted with a connector 24 such that the second end 16 of the airway tube 12 can be connected to the relevant gas supply. The airway device 10 also has a shoulder 26. The shoulder 26 is used to prevent over-insertion of the airway device 10. The shoulder 26 is located laterally or perpendicular to the direction of the airflow, and thus the airway tube 12. The shoulder 26 is located just above the neck 28 of the airway device 10 where the laryngeal cuff 18 appears to join the airway tube 12 at the second end 14. The shoulder 26 is used to create a point of contact between the airway device 10 and the faucial pillars located at the back of the mouth of a human or animal patient. This thus creates a positive stopping feature that in use prevents the shoulder 26 going forward beyond the faucial pillars of the patient to prevent over-insertion of the airway device 10.

The airway device 10 is further provided with a raised portion 38, which is formed from a material, such as a polymeric or other plastics material with a Shore hardness between 80 and 000 on the A scale. The raised portion 38 is located on the airway tube 12 above and extending just behind the shoulder 26 towards the second end 16 of the airway tube. When in situ in a patient, the raised portion 38 corresponds to location of the cavity of the upper mouth arch of the patient called the palatoglossal arch. The raised portion 38 aids in preventing over-insertion of the airway device 10 by being adapted to locate in the cavity of the palatoglossal arch due to the contouring of the raised portion and provides resistance from being moved beyond this position.

The airway device 10 is also further provided with a plurality of ribs 60 near the second end 16 of the airway tube 12 near to the connector 24. The ribs 60 provide a friction point for tying the device around an animal's head as it is generally not possible to use tape as in humans due to the animal's fur.

The tip 32 of the laryngeal cuff is provided with an annular sealing bulge 90.

The annular sealing bulge 90 is provided for improved sealing of the tip 32 of the laryngeal cuff 18 in the upper oesophagus region of the human or animal patient. The annular sealing bulge 90 is formed from a soft polymeric or other plastics material with a Shore hardness of between 40 and 000 on the A scale. The annular sealing bulge 90 allows for better sealing with a more variable range of upper oesophageal anatomical features. In the embodiment illustrated the annular sealing bulge 90 is larger on the front face portion of the tip 32 than on the dorsal portion of the tip. The unsymmetrical nature of the annular sealing bulge 90 means that should the human or animal patient regurgitate or vomit whilst the airway device is in situ in the human or animal patient the regurgitate or vomit, if not completely stopped by the annular sealing bulge 90, is more likely to take the path of least resistance i.e. via the dorsal portion of the tip and the airway device rather than the front face portion of the tip and thus the airway device. This is safer for the human or animal patient as this means that it is less likely for the regurgitate or vomit to enter into the airway of the human or animal patient. In an alternative, the annular sealing bulge 90 on the front face portion of the tip may be provided with a inner core formed from a rigid material covered or coated with a soft polymeric or other plastics material with a Shore hardness of between 40 and 000 on the A scale.

The airway device 10 is also provided with a concave portion or scallop 96 on the airway tube 12. The concave portion or scallop 96 is located on the opposite side of the airway tube 12 to the raised portion 38 around the location of the shoulder 26. The concave portion of scallop 96 is located at the back of the tongue of the patient in use. The concave portion or scallop 96 acts to reduce the amount of pressure being applied to the convex portion of back of the tongue. When pressure is applied to the convex portion at the back of the tongue, this results in the formation of blue tongue in patients because the pressure to the tongue constricts blood vessels.

Figure 9:
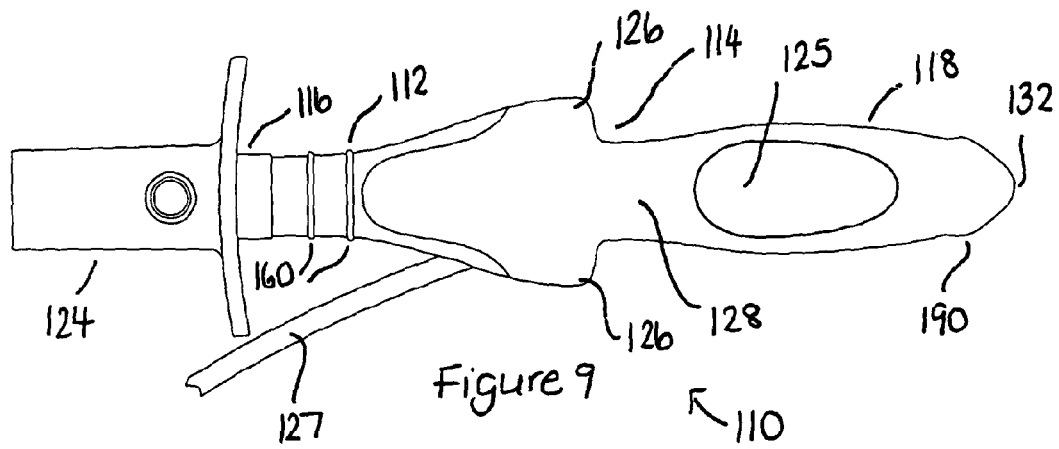
FIG. 9 is a top view of an airway device according to a second embodiment of the present invention.
Figure 10:
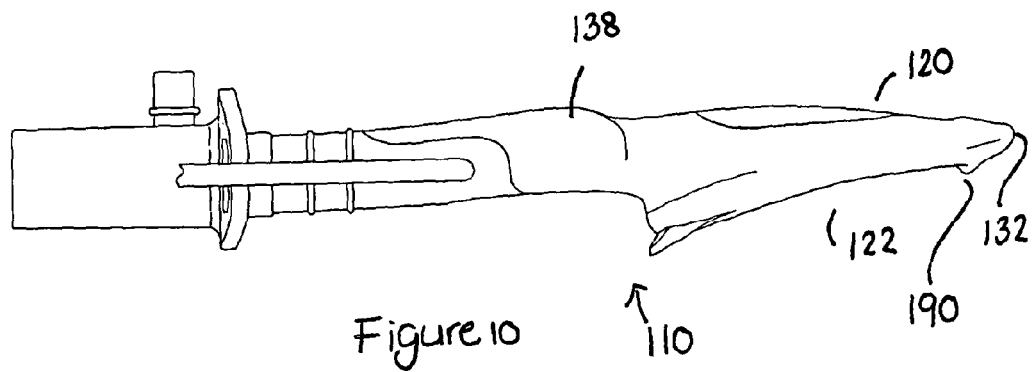
FIG. 10 is a right side view of an airway device according to a second embodiment of the present invention.
Figure 11:
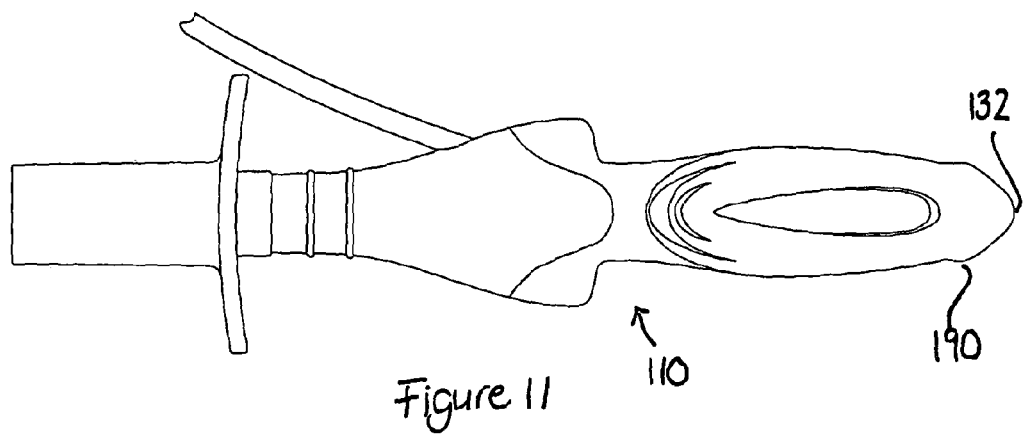
FIG. 11 is a bottom view of an airway device according to a second embodiment of the present invention.
Figure 12:
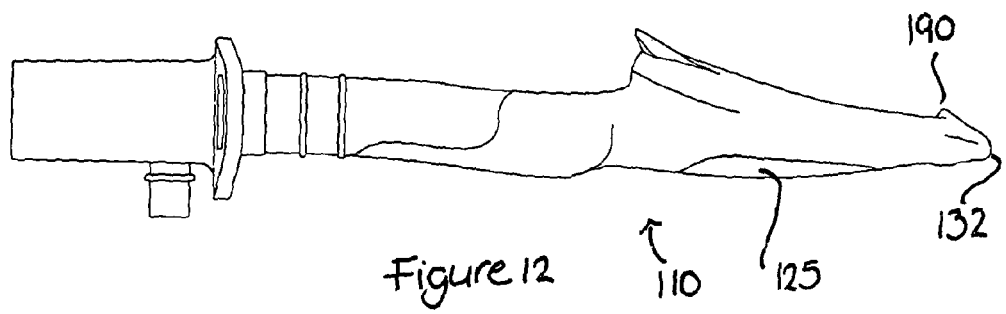
FIG. 12 is a left side view of an airway device according to a second embodiment of the present invention.
Figure 13:
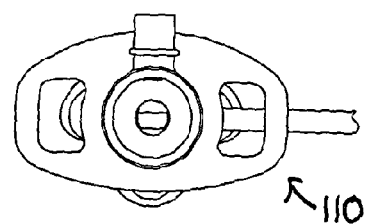
FIG. 13 is a rear view of an airway device according to a second embodiment of the present invention.
Figure 14:
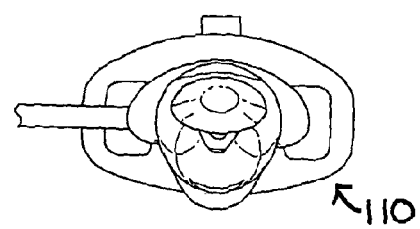
FIG. 14 is a front view of an airway device according to a second embodiment of the present invention.
Figure 15:
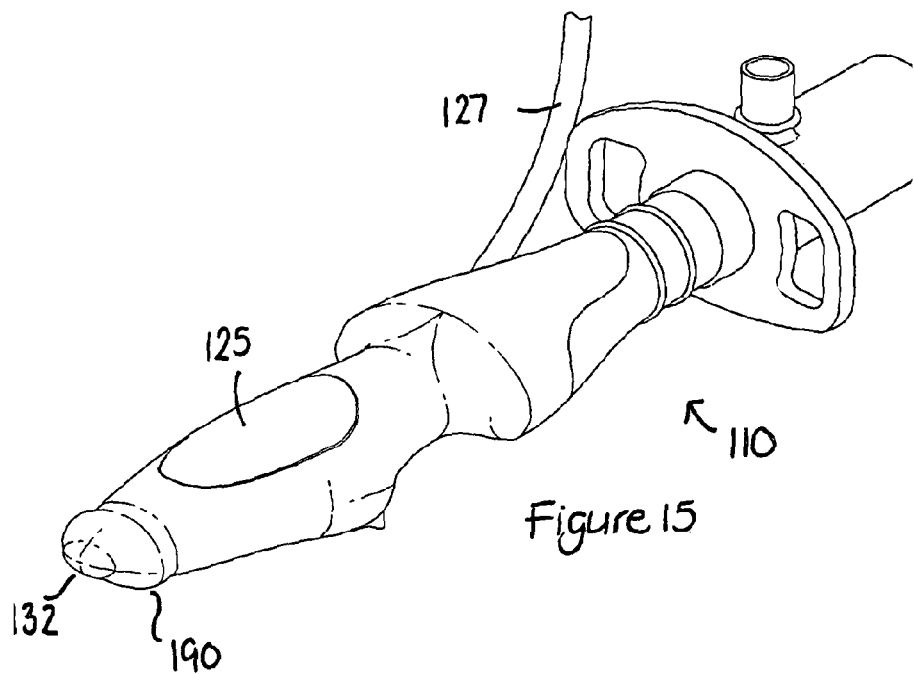
FIG. 15 is a top perspective view of an airway device according to a second embodiment of the present invention.
Figure 16:
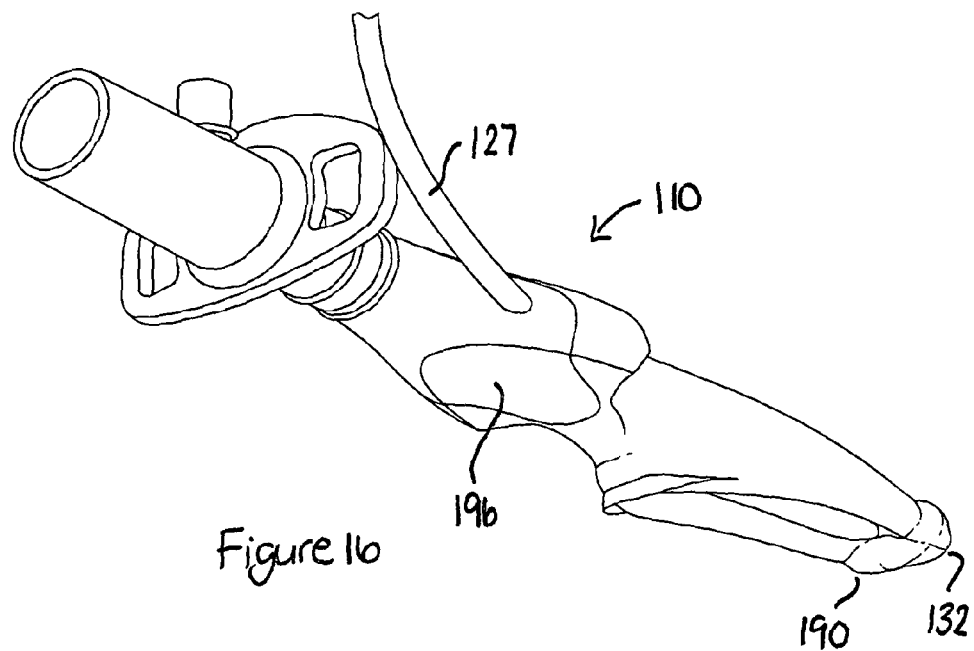
FIG. 16 is a bottom perspective view of an airway device according to a second embodiment of the present invention.

FIGS. 9 to 16 illustrate a second embodiment of an airway device 110 according to the present invention. The airway device 110 has an airway tube 112 with a first end 114 and a second end 116. The first end 114 of the airway tube 112 is surrounded by a laryngeal cuff 118. The cuff 118 has a back dorsal portion 120 and a front face portion 122. The front face portion 122 is shaped to form an anatomical fit over the laryngeal inlet of a human or animal patient. The second end 116 of the airway tube is fitted with a connector 124 such that the second end 116 of the airway tube 112 can be connected to the relevant gas supply. The airway device 110 also has a shoulder 126. The shoulder 126 is used to prevent over-insertion of the airway device 110. The shoulder 126 is located laterally and substantially perpendicular to the direction of the airflow, and thus the airway tube 112. The shoulder 126 is located just above the neck 128 of the airway device 110 where the laryngeal cuff 118 appears to join the airway tube 112 at the second end 114. The shoulder 126 is used to create a point of contact between the airway device 3110 and the faucial pillars located at the back of a human or animal patient. This thus creates a positive stopping feature that in use prevents the shoulder portion 126 going forward beyond the faucial pillars of the patient and thus prevents over-insertion of the airway device 110.

The airway device 110 is further provided with a raised portion 138. The raised portion 138 is located on the airway tube 112 above and extending just behind the shoulder 126 towards the second end 116 of the airway tube, when in situ in the patient, the raised portion 138 corresponds to the location of the cavity of the upper mouth arch of the patient called the palatoglossal arch. The raised portion 138 aids in preventing over-insertion of the airway device by being adapted to locate in the cavity of the palatoglossal arch due to the contouring of the raised portion and provides resistance on being moved beyond this position. The raised portion 138 is not meant to be in constant contact with the palatoglossal arch but simply to locate into this cavity to prevent over-insertion and resist movement of the device when in situ.

The airway device 110 is also further provided with a plurality of ribs 160 near the second end 116 of the airway tube 112 near to the connector 124. The ribs 160 provide a friction point for tying the device around an animal's head as it is generally not possible to use tape as in humans due to the animal's fur.

The tip 132 of the laryngeal cuff 118 is also provided with an annular sealing bulge 190. The annular sealing bulge 190 is provided for improved sealing of the tip 132 of the laryngeal cuff 118 in the upper oesophagus region of the human or animal patient. The annular sealing bulge is formed of a soft polymeric or other plastics material with a shore hardness of between 40 and 000 on the A scale. The annular sealing bulge 190 allows for better sealing with a more variable range of upper oesophageal features. In the embodiment illustrated the annular sealing bulge 190 is larger on the front face portion of the tip 132 than on the dorsal portion of the tip. The unsymmetrical nature of the annular sealing bulge 190 means that should the human or animal patient regurgitate or vomit whilst the airway device is in situ in the human or animal patient the regurgitate or vomit, if not completely stopped by the annular sealing bulge 190, is more likely to take the path of least resistance i.e. via the dorsal portion of the tip and the airway device rather than the front face portion of the tip and thus the airway device. This is safer for the human or animal patient as this means that it is less likely for the regurgitate or vomit to enter into the airway of the human or animal patient. In an alternative, the annular sealing bulge 190 on the front face portion of the tip may be provided with an inner core formed from a rigid material covered or coated with a soft polymeric or other plastics material with a Shore hardness of between 40 and 000 on the A scale.

The airway device 110 is also provided with a concave portion or scallop 196 on the airway tube 112. The concave portion or scallop 196 is located on the opposite side of the airway tube 112 to the raised portion 138 around the location of the shoulder 126. The concave portion of scallop 196 is located at the back of the tongue of the patient in use. The concave portion or scallop 196 acts to reduce the amount of pressure being applied to the convex portion of back of the tongue. When pressure is applied to the convex portion at the back of the tongue, this results in the formation of blue tongue in patients because the pressure to the tongue constricts blood vessels.

In addition the airway device 110 according to the second embodiment of the present invention is further provided with an inflatable back cuff 125 and inflation line 127 to inflate the inflatable back cuff 125. The inflatable back cuff 125 is designed to lay flush with the profile of the back dorsal portion 120 of the laryngeal cuff 118 when not inflated, such that the inflatable back cuff 125 does not interfere with the insertion of the device 110. The inflatable back cuff 125 is provided to give flexibility of fit of the device in different patients.

Figure 21:
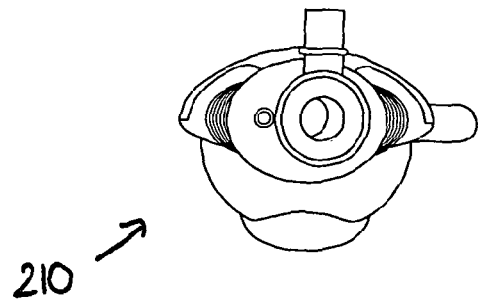
FIG. 21 is a rear view of an airway device according to a third embodiment of the present invention.
Figure 22:
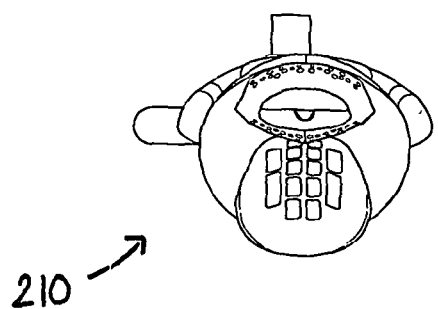
FIG. 22 is a front view of an airway device according to a third embodiment of the present invention.
Figure 23:
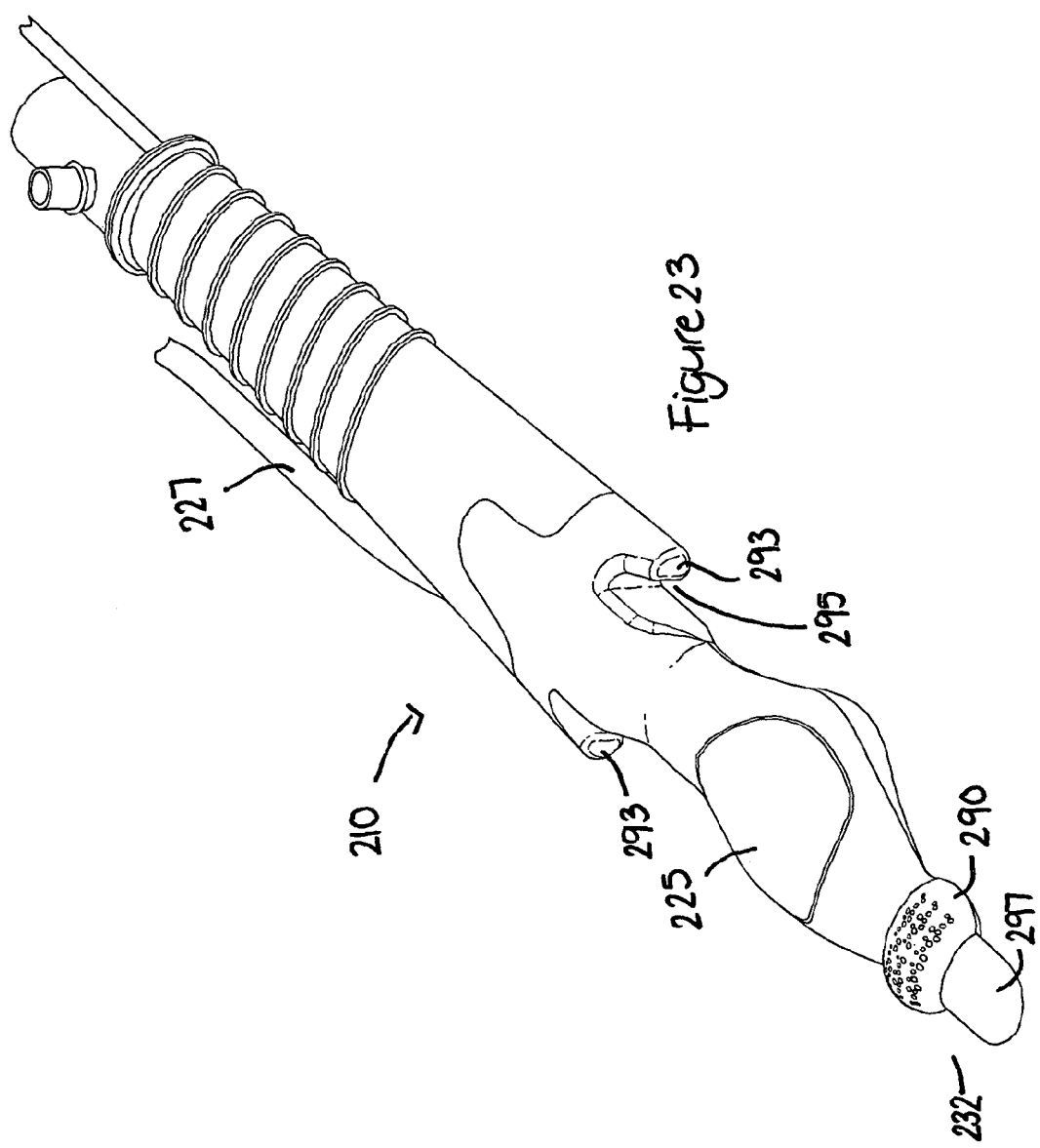
FIG. 23 is a top perspective view of an airway device according to a third embodiment of the present invention.
Figure 24:
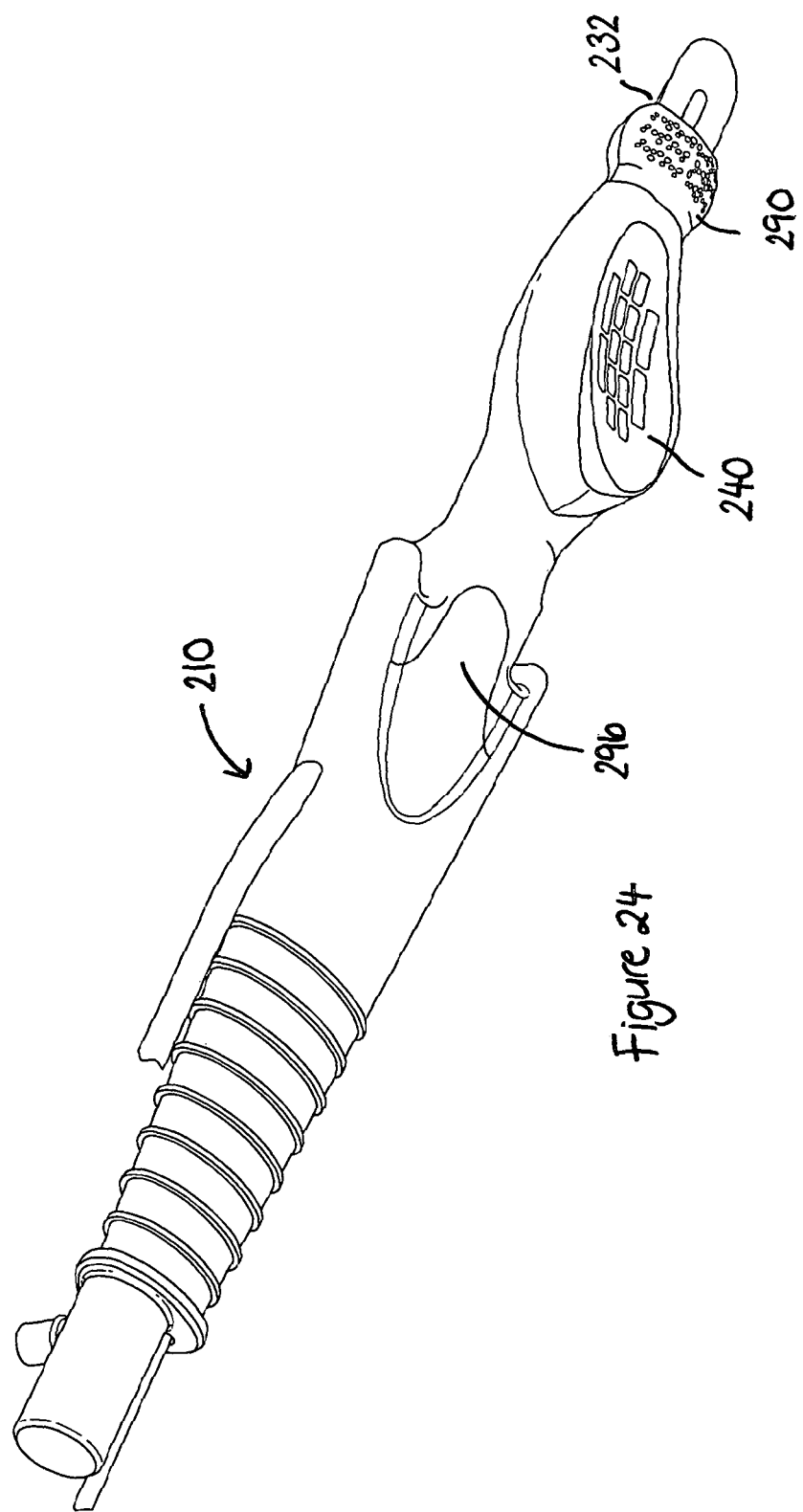
FIG. 24 is a bottom perspective view of an airway device according to a third embodiment of the present invention.

FIGS. 17 to 24 illustrate a third embodiment of an airway device 210. The airway device 210 has an airway tube 212 with a first end 214 and a second end 216. The first end 214 of the airway tube 212 is surrounded by a laryngeal cuff 218. The cuff 218 has a back dorsal portion 220 and a front face portion 222. The front face portion 222 is shaped to form an anatomical fit over the laryngeal inlet of a human or animal patient. The second end 216 of the airway tube is fitted with a connector 224 such that the second end 216 of the airway tube 212 can be connected to the relevant gas supply. The airway device 210 also has a shoulder 226. The shoulder 226 is used to prevent over-insertion of the airway device 210. The shoulder 226 is located laterally and substantially perpendicular to the direction of the airflow, and thus the airway tube 212. The shoulder 226 is located just above the neck 228 of the airway device 210 where the laryngeal cuff 218 appears to join the airway tube 212 at the second end 214. The shoulder 226 is used to create a point of contact between the airway device 210 and the faucial pillars located at the back of the patient's mouth. This thus creates a positive stopping feature that in use prevents the shoulder portion 226 going forward beyond the faucial pillars of the patient and thus prevents over-insertion of the airway device 210.

In addition the airway device 210 the shoulder 226 is provided with forward facing protrusions 293 located on the leading edge thereof. The forward facing protrusions 293 are adapted to locate into anatomical cavities which are present in some species of animal, after the pharyngeal arches. Dogs for example tend to have a very wide pharyngeal arch as they are designed to consume large volumes of food very rapidly. The forward facing protrusions 293 being adapted to fit into the anatomical cavity region to make the whole airway device 210 fit more securely and not easily by-pass the pharyngeal arches. It is worth bearing in mind that the pharyngeal arches are particularly elastic in dogs for example. Cavities 295 are adapted to fit the thin protruding pharyngeal arches of the patient, if present, without which the shoulders 226 may be able to extend beyond in some species of animal.

The airway device 210 is further provided with a raised portion 238. The raised portion 238 is located on the airway tube 212 above and extending just behind the shoulder 226 towards the second end 216 of the airway tube when in situ in the patient, the raised portion 238 corresponds to the location of the cavity of the upper mouth arch of the patient called the palatoglossal arch. The raised portion 238 aids in preventing over-insertion of the airway device by being adapted to locate in the cavity of the palatoglossal arch due to the contouring of the raised portion and provides resistance on being moved beyond this position. The raised portion 238 is not meant to be in constant contact with the palatoglossal arch but simply to locate into this cavity to prevent over-insertion and resist movement of the device when in situ.

The airway device 210 is also further provided with a plurality of ribs 260 near the second end 216 of the airway tube 212 near to the connector 224. The ribs 260 provide a friction point for tying the device around an animal's head as it is generally not possible to use tape as in humans due to the animal's fur.

In this embodiment the tip 232 is a blade like tip 297. The blade like tip 297 is curved on the dorsal portion of the tip 223 and planar on the front face portion of the tip 251. The blade like tip 297 is used to "flick" or peel the epiglottis of the dog downwards at the same time as the airway device 210 is inserted in a single action.

The tip 232 of the laryngeal cuff 218 is also provided with an annular sealing bulge 290. The annular sealing bulge 290 is provided for improved sealing of the tip 232 of the laryngeal cuff 218 in the upper oesophagus region of the patient. The annular sealing bulge is formed of a soft polymeric or other plastics material with a shore hardness of between 40 and 000 on the A scale. The annular sealing bulge 290 allows for better sealing with a more variable range of upper oesophageal features. The annular sealing bulge 290 is further provided with a dimpled surface. The dimpled surface reduces the surface area of the annular sealing bulge 290 that is in contact with the upper oesophageal features of the patient when in situ in the patent to reduce trauma resulting from contact between the bulge 290 and such features whilst still creating a good seal therewith.

The airway device 210 is also provided with a concave portion or scallop 296 on the airway tube 212. The concave portion or scallop 296 is located on the opposite side of the airway tube 212 to the raised portion 238 around the location of the shoulder 226. The concave portion of scallop 296 is located at the back of the tongue of the human or animal patient in use. The concave portion or scallop 296 acts to reduce the amount of pressure being applied to the convex portion of back of the tongue. When pressure is applied to the convex portion at the back of the tongue, this results in the formation of blue tongue in patients because the pressure to the tongue constricts blood vessels.

In addition the airway device 210 according to the third embodiment of the present invention is further provided with an inflatable back cuff 225 and inflation line 227 to inflate the inflatable back cuff 225. The inflatable back cuff 225 is designed to lay flush with profile of the back dorsal portion 220 of the laryngeal cuff 218 when not inflated, and this does not interfere with the insertion of the device 210. The inflatable back cuff 225 is provided to give flexibility of fit of the device in different patients.

Furthermore the airway device 210 is provided with an oesophageal gastric channel 280.

Finally in this embodiment a membrane 240 with a plurality of apertures has been provided. The membrane 240 is provided to prevent the epiglottis of the patient from occluding the airway if the epiglottis should become downfolded.

Figure 25:
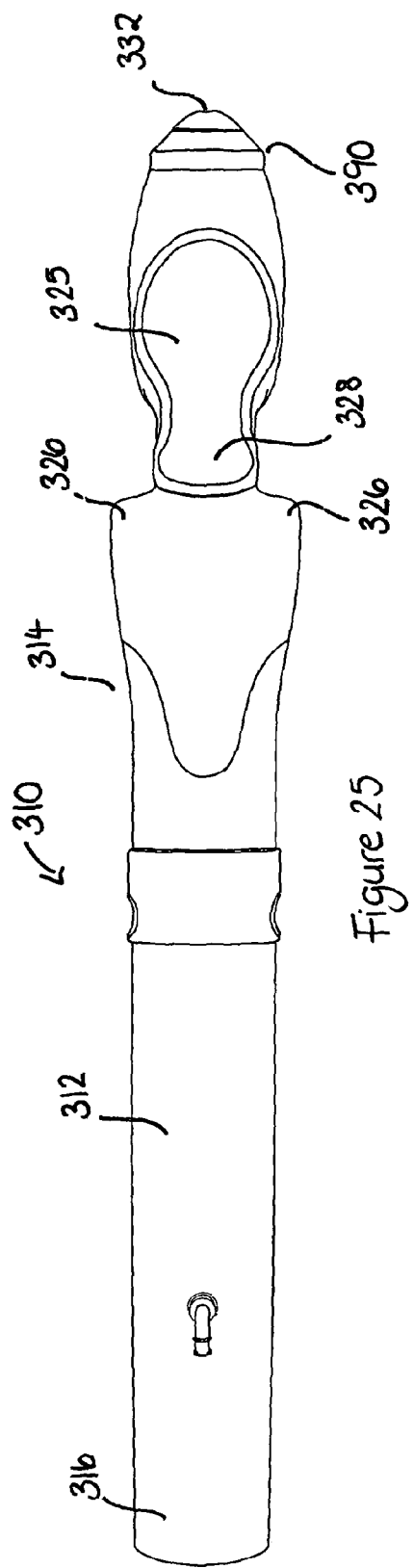
Figure 26:
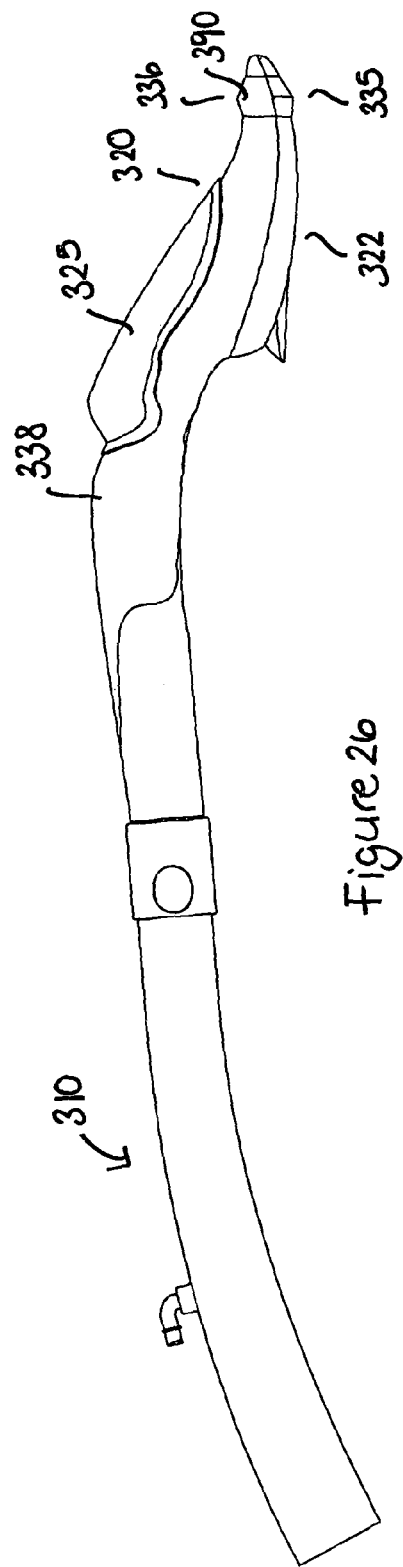
Figure 27:
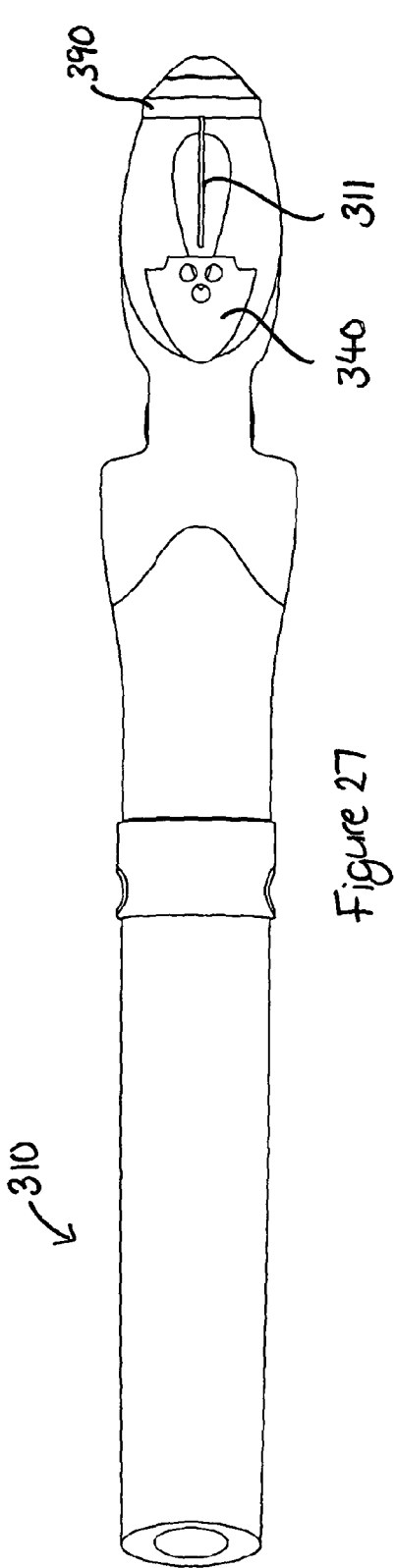
Figure 28:
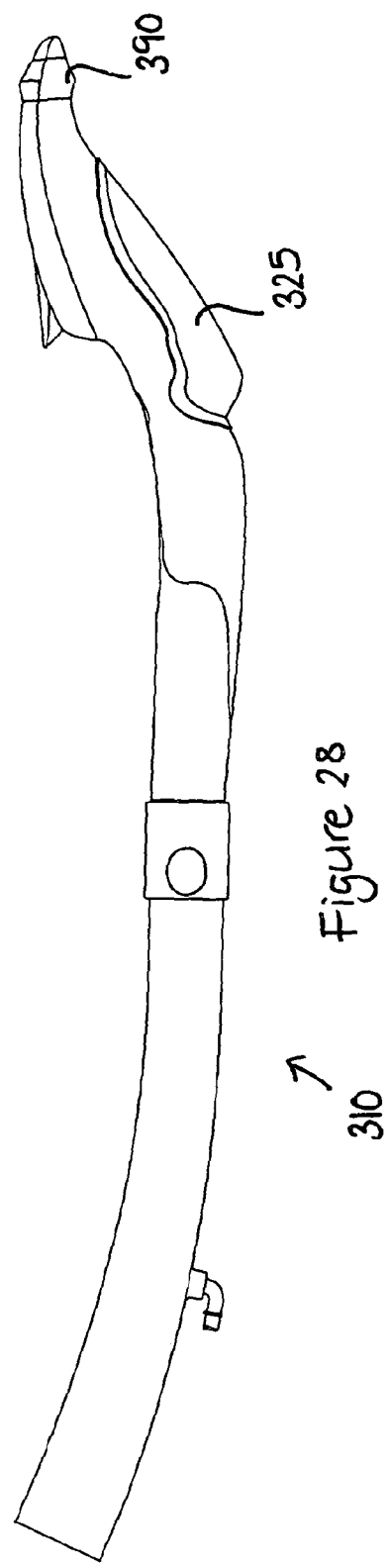
Figure 29:
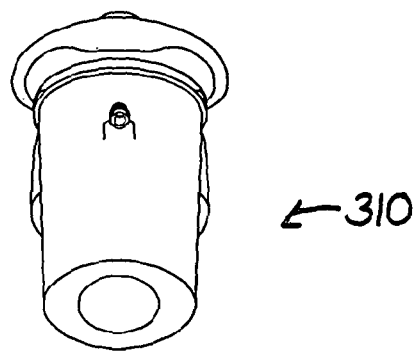
Figure 30:
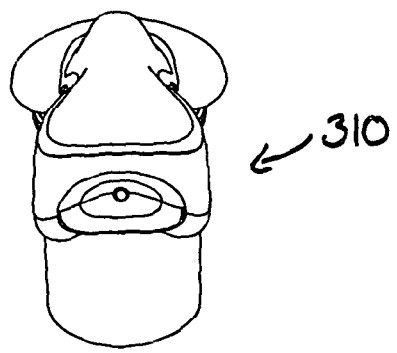
Figure 31:
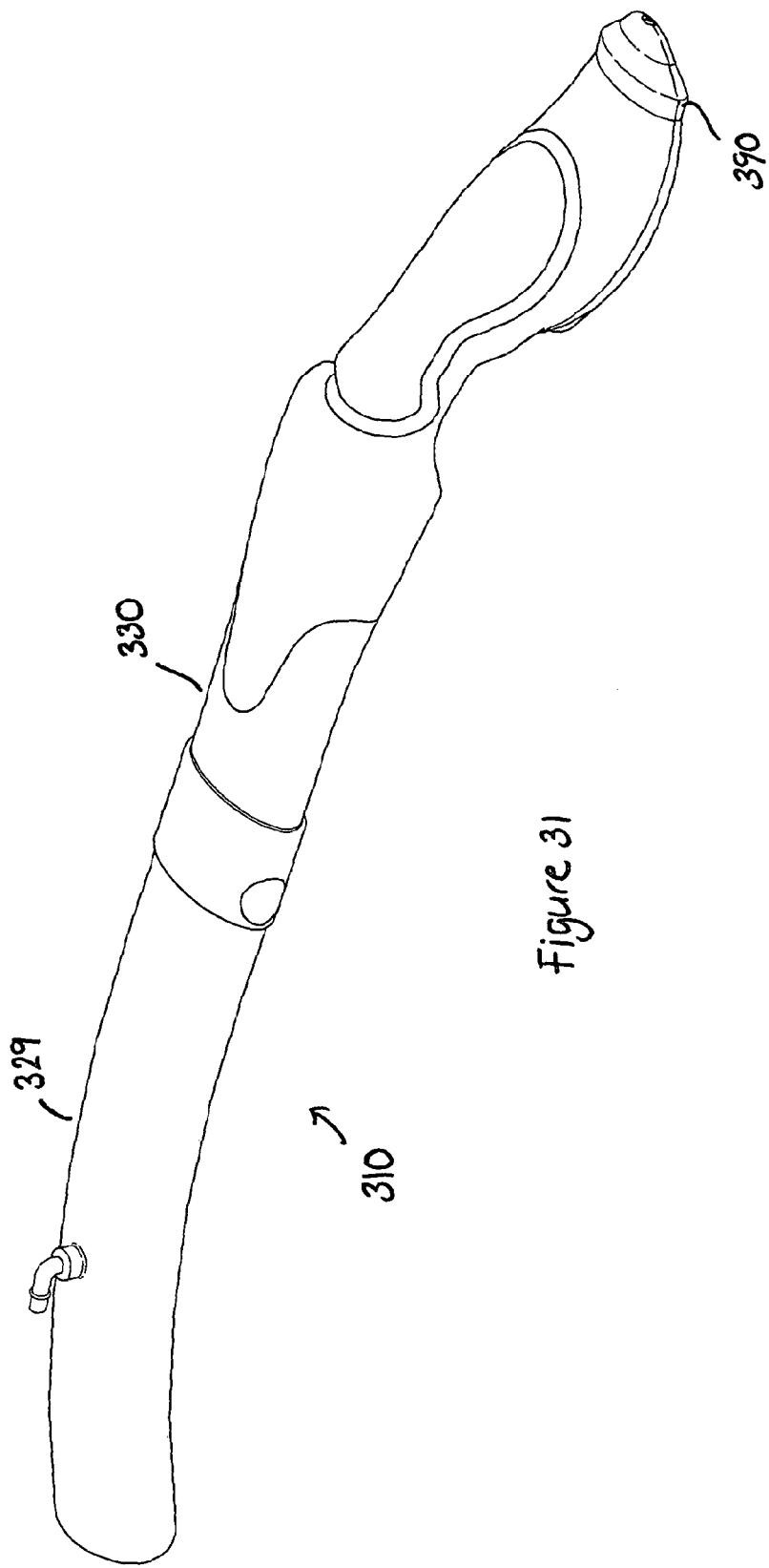
Figure 32:
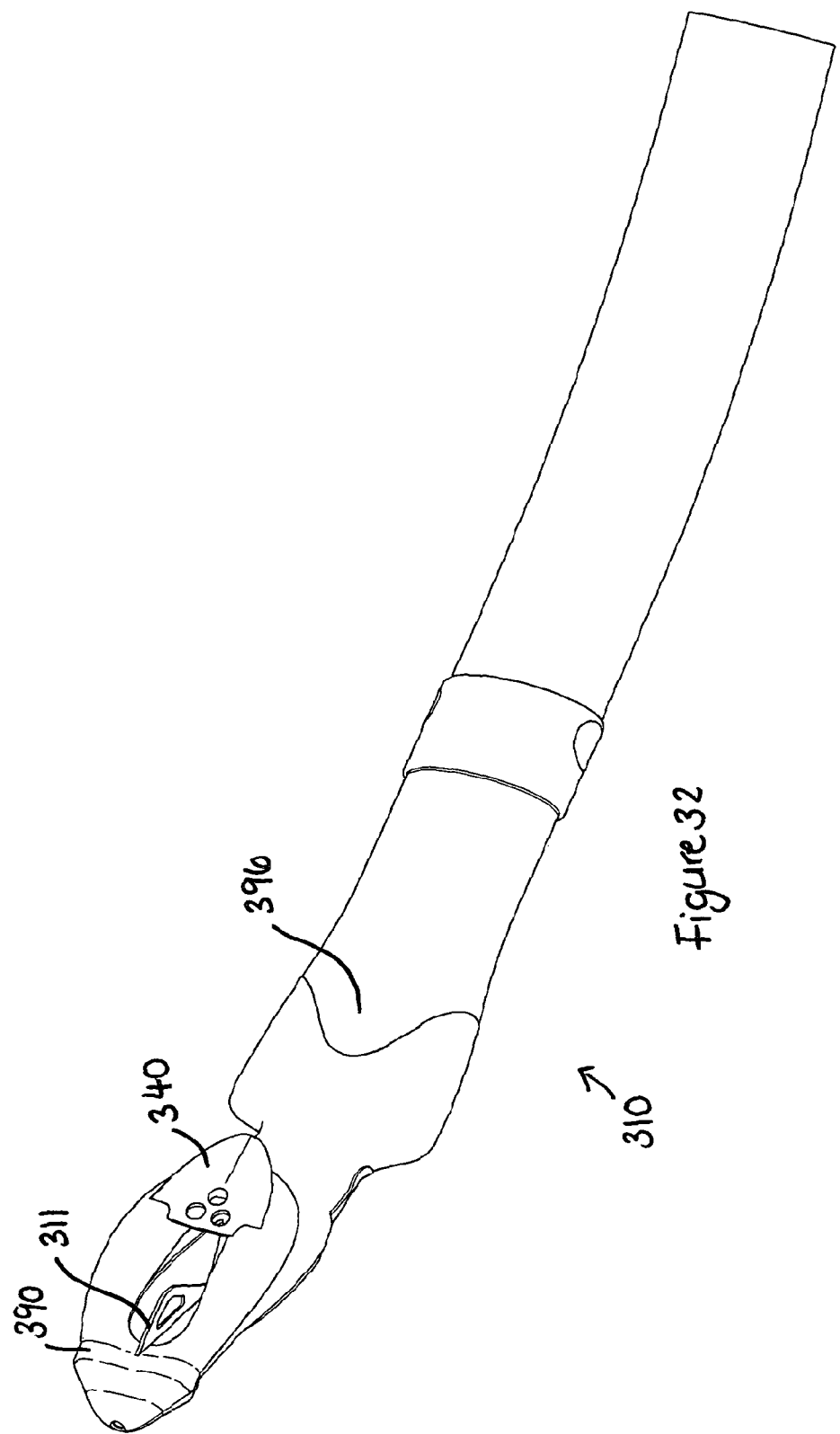

FIGS. 25 to 32 illustrate a fourth an embodiment of the airway device 310. The airway device 310 has an airway tube 312 with a first end 314 and a second end 316. The first end 314 of the airway tube 312 is surrounded by a laryngeal cuff 318. The cuff 318 has a back dorsal portion 320 and a front face portion 322. The front face portion 322 is shaped to form an anatomical fit over the laryngeal inlet of a patient. The second end 316 of the airway tube is fitted with a connector (not shown) such that the second end 316 of the airway tube 312 can be connected to the relevant gas supply. The airway device 310 also has a shoulder 326. The shoulder 326 is used to prevent over-insertion of the airway device 310. The shoulder 326 is located laterally and substantially perpendicular to the direction of the airflow, and thus the airway tube 312. The shoulder 326 is located just above the neck 328 of the airway device 310 where the laryngeal cuff 318 appears to join the airway tube 312 at the second end 314. The shoulder 326 is used to create a point of contact between the airway device 310 and the faucial pillars located at the back of the patient's mouth. This thus creates a positive stopping feature that in use prevents the shoulder portion 326 going forward beyond the faucial pillars of the patient and thus prevents over-insertion of the airway device 310.

The airway device 310 is further provided with a raised portion 338. The raised portion 338 is located on the airway tube 312 above and extending just behind the shoulder 326 towards the second end 316 of the airway tube, when in situ in the patient, the raised portion 338 corresponds to the location of the cavity of the upper mouth arch of the patient called the palatoglossal arch. The raised portion 338 aids in preventing over-insertion of the airway device by being adapted to locate in the cavity of the palatoglossal arch due to the contouring of the raised portion and provides resistance on being moved beyond this position. The raised portion 338 is not meant to be in constant contact with the palatoglossal arch but simply to locate into this cavity to prevent over-insertion and resist movement of the device when in situ.

In order to further discourage over-insertion, the tip 332 of the laryngeal cuff 318 is angled upwards away from the horizontal plane of the laryngeal cuff 318. The tip 332 may be angled from 5° to 80°. The angle of the tip 332 has the effect of increasing the surface area of the tip 332. The tip 332 engages to seal with the top of the oesophagus of the patient when the airway device 310 is correctly inserted. The larger tip 332 surface area creates some resistance with the top of the oesophagus during insertion which would be felt by the clinician during insertion to determine that the airway 310 device has been correctly inserted. The tip is formed from materials of two different hardnesses. A soft material is used for the front face portion of the tip 334 and a harder material is used for the rear dorsal portion of the tip 336. This results in a tip which has strength to prevent the tip folding over on itself and soft to prevent damage to the oesophagus upon contact.

The tip 332 of the laryngeal cuff 318 is also provided with an annular sealing bulge 390. The annular sealing bulge 390 is provided for improved sealing of the tip 332 of the laryngeal cuff 318 in the upper oesophagus region of the patient. The annular sealing bulge is formed of a soft polymeric or other plastics material with a shore hardness of between 40 and 000 on the A scale. The annular sealing bulge 390 allows for better sealing with a more variable range of upper oesophageal features.

The airway device 310 is also provided with a concave portion or scallop 396 on the airway tube 312. The concave portion or scallop 396 is located on the opposite side of the airway tube 312 to the raised portion 338 around the location of the shoulder 326. The concave portion of scallop 396 is located at the back of the tongue of the patient in use. The concave portion or scallop 396 acts to reduce the amount of pressure being applied to the convex portion of back of the tongue. When pressure is applied to the convex portion at the back of the tongue, this results in the formation of blue tongue in patients because the pressure to the tongue constricts blood vessels.

In addition the airway device 310 is further provided with an inflatable back and neck cuff 325 and inflation line (not shown) to inflate the inflatable back and neck cuff 325. The inflatable back and neck cuff 325 is designed to lay flush with profile of the back dorsal portion 320 of the laryngeal cuff 318 when not inflated, and this does not interfere with the insertion of the device 310. The inflatable back and neck cuff 325 is provided to give flexibility of fit of the device in different patients. The inflatable back and neck cuff 325 when inflated is adapted to expand to fit into the large void area in horses for example which would otherwise might lead to a reduced seal of the laryngeal cuff around the laryngeal inlet of the patient.

Furthermore the distal opening of the cuff 318 is provided with a bracket 311 to provide strength to the tip 332 of the device 310 and to prevent downfolding of the patient's epiglottis into the opening of the cuff and blocking the air flow.

The airway tube 312 is designed in two portions 329 and 330 such that the device 310 can be split into two portions to fit into standard sized autoclaves for sterilization between uses.

The airway device 310 is further provided with an epiglottic membrane rest 340 provided with a plurality of apertures. The epiglottic membrane rest 340 is adapted to prevent the epiglottis of the patient from occluding the airway if the epiglottis should become downfolded.

Figure 33:
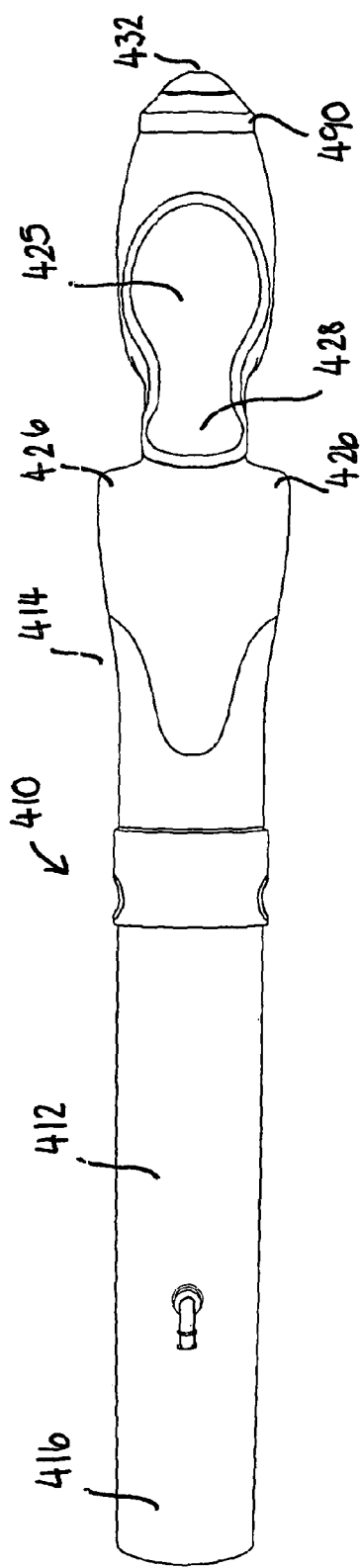
Figure 34:
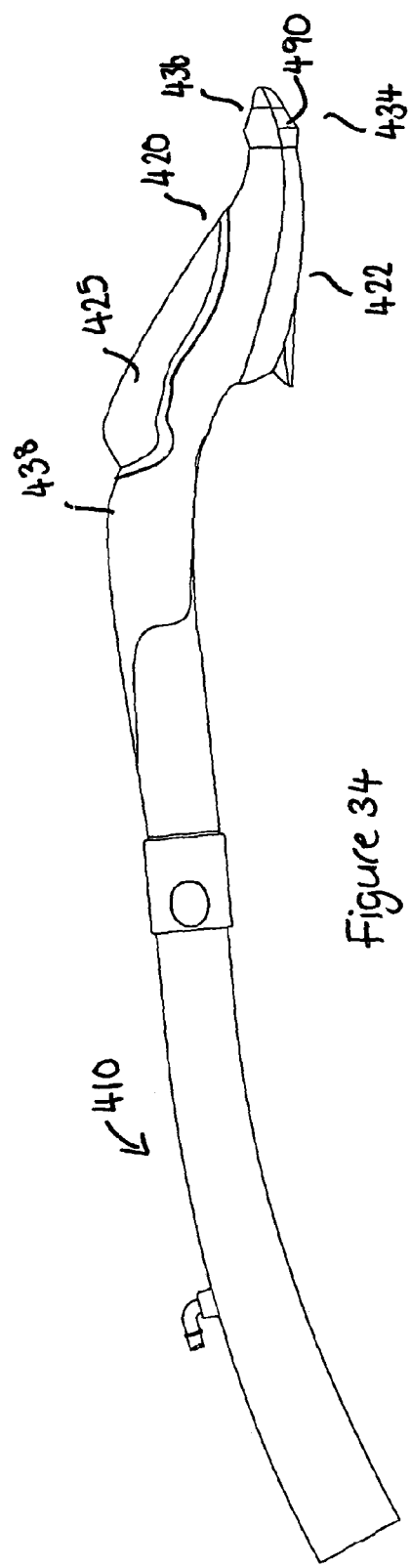
Figure 35:
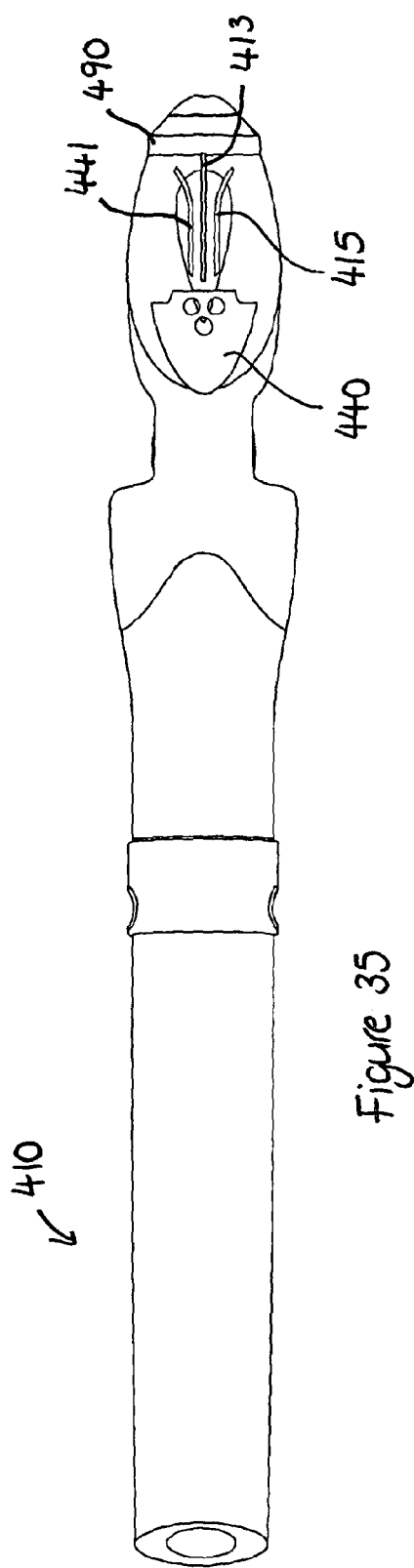
Figure 36:
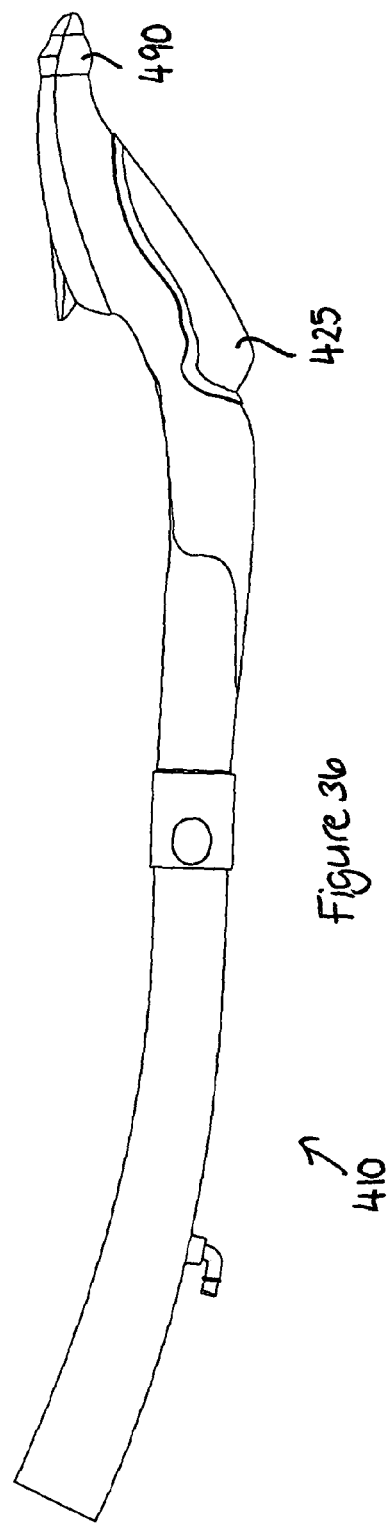
Figure 37:
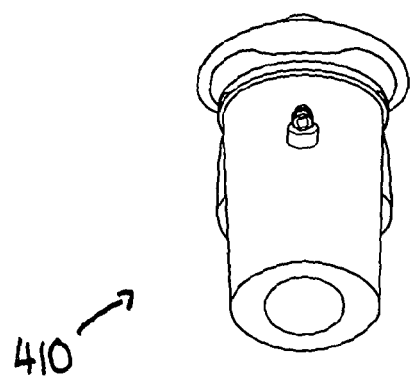
Figure 38:
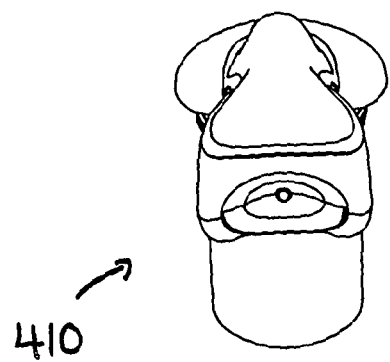
Figure 39:
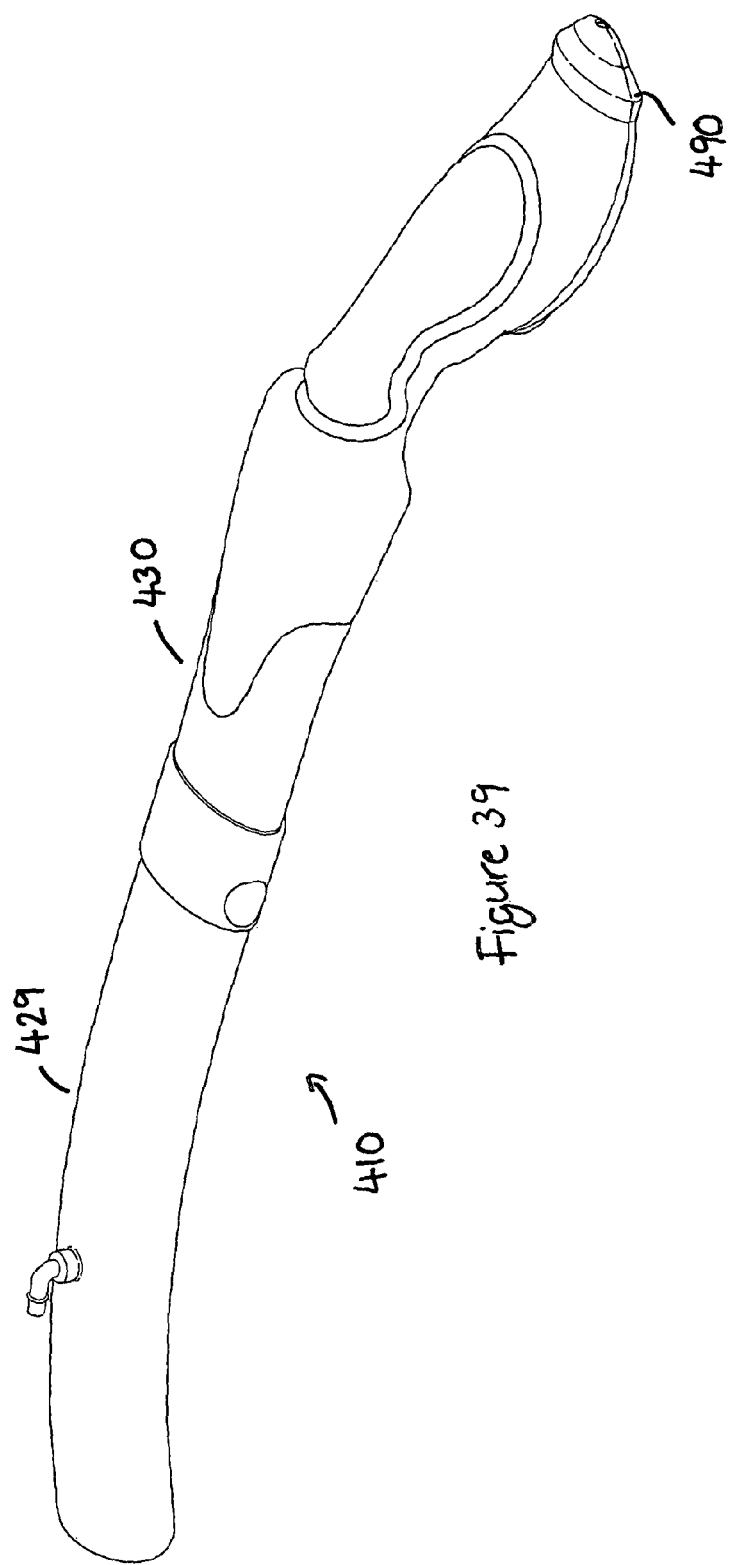
Figure 40:
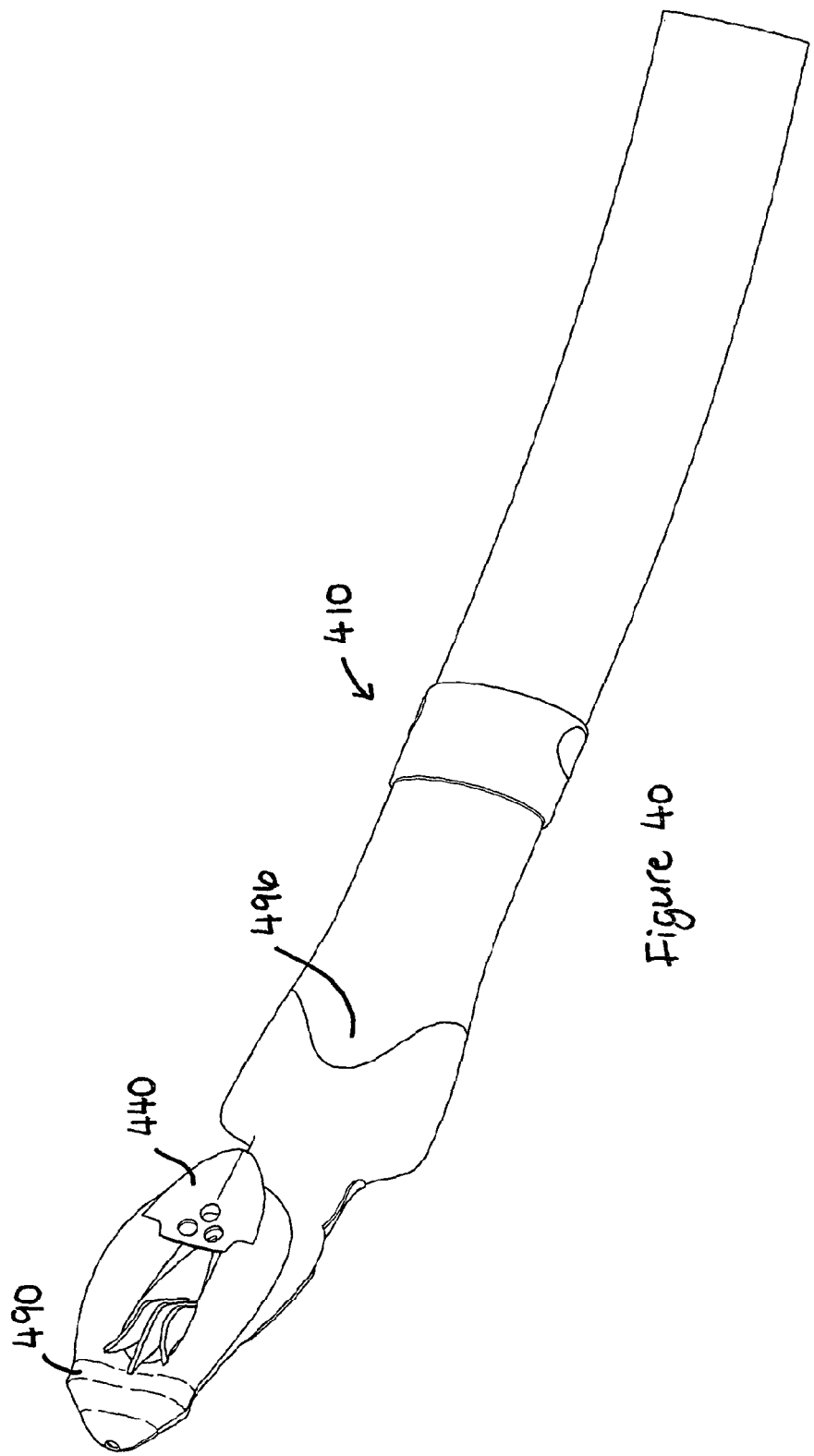

FIGS. 33 to 40 illustrate a fifth an embodiment of the airway device 410. The airway device 410 has an airway tube 412 with a first end 414 and a second end 416. The first end 414 of the airway tube 412 is surrounded by a laryngeal cuff 418. The cuff 418 has a back dorsal portion 420 and a front face portion 422. The front face portion 422 is shaped to form an anatomical fit over the laryngeal inlet of a patient. The second end 416 of the airway tube is fitted with a connector (not shown) such that the second end 416 of the airway tube 412 can be connected to the relevant gas supply. The airway device 410 also has a shoulder 426. The shoulder 426 is used to prevent over-insertion of the airway device 410. The shoulder 426 is located laterally and substantially perpendicular to the direction of the airflow, and thus the airway tube 412. The shoulder 426 is located just above the neck 428 of the airway device 410 where the laryngeal cuff 418 appears to join the airway tube 412 at the second end 414. The shoulder 426 is used to create a point of contact between the airway device 410 and the faucial pillars located at the back of the patient's mouth. This thus creates a positive stopping feature that in use prevents the shoulder portion 426 going forward beyond the faucial pillars of the patient and thus prevents over-insertion of the airway device 410.

The airway device 410 is further provided with a raised portion 438. The raised portion 438 is located on the airway tube 412 above and extending just behind the shoulder 426 towards the second end 416 of the airway tube, when in situ in the patient, the raised portion 438 corresponds to the location of the cavity of the upper mouth arch of the patient called the palatoglossal arch. The raised portion 438 aids in preventing over-insertion of the airway device by being adapted to locate in the cavity of the palatoglossal arch due to the contouring of the raised portion and provides resistance on being moved beyond this position. The raised portion 438 is not meant to be in constant contact with the palatoglossal arch but simply to locate into this cavity to prevent over-insertion and resist movement of the device when in situ.

In order to further discourage over-insertion, the tip 432 of the laryngeal cuff 418 is angled upwards away from the horizontal plane of the laryngeal cuff 418. The tip 432 may be angled from 5° to 80°. The angle of the tip 432 has the effect of increasing the surface area of the tip 432. The tip 432 engages to seal with the top of the oesophagus of the patient when the airway device 410 is correctly inserted. The larger tip 432 surface area creates some resistance with the top of the oesophagus during insertion which would be felt by the clinician during insertion to determine that the airway 410 device has been correctly inserted. The tip is formed from materials of two different hardnesses. A soft material is used for the front face portion of the tip 434 and a harder material is used for the rear dorsal portion of the tip 436. This results in a tip which has strength to prevent the tip folding over on itself and soft to prevent damage to the oesophagus upon contact.

The tip 432 of the laryngeal cuff 418 is also provided with an annular sealing bulge 490. The annular sealing bulge 490 is provided for improved sealing of the tip 432 of the laryngeal cuff 418 in the upper oesophagus region of the patient. The annular sealing bulge is formed of a soft polymeric or other plastics material with a shore hardness of between 40 and 000 on the A scale. The annular sealing bulge 490 allows for better sealing with a more variable range of upper oesophageal features.

The airway device 410 is also provided with a concave portion or scallop 496 on the airway tube 412. The concave portion or scallop 496 is located on the opposite side of the airway tube 412 to the raised portion 438 around the location of the shoulder 426. The concave portion of scallop 496 is located at the back of the tongue of the patient in use. The concave portion or scallop 496 acts to reduce the amount of pressure being applied to the convex portion of back of the tongue. When pressure is applied to the convex portion at the back of the tongue, this results in the formation of blue tongue in patients because the pressure to the tongue constricts blood vessels.

In addition the airway device 410 is further provided with an inflatable back and neck cuff 425 and inflation line (not shown) to inflate the inflatable back and neck cuff 425. The inflatable back and neck cuff 425 is designed to lay flush with profile of the back dorsal portion 420 of the laryngeal cuff 418 when not inflated, and this does not interfere with the insertion of the device 410. The inflatable back and neck cuff 425 is provided to give flexibility of fit of the device in different patients. The inflatable back and neck cuff 425 when inflated is adapted to expand to fit into the large void area in horses for example which would otherwise lead to a reduced seal of the laryngeal cuff around the laryngeal inlet of the patient.

Furthermore the distal opening of the cuff 418 is provided with a series of brackets 411, 413, 415 to provide strength to the tip 432 of the device 410 and to prevent downfolding of the patient's epiglottis into the opening of the cuff and blocking the air flow.

The airway tube 412 is designed in two portions 429 and 430 such that the device 410 can be split into two portions to fit into standard sized autoclaves for sterilization between uses.

The airway device 410 is further provided with an epiglottic membrane rest 440 provided with a plurality of apertures. The epiglottic membrane rest 440 is adapted to prevent the epiglottis of the patient from occluding the airway if the epiglottis should become downfolded.

Figure 45:
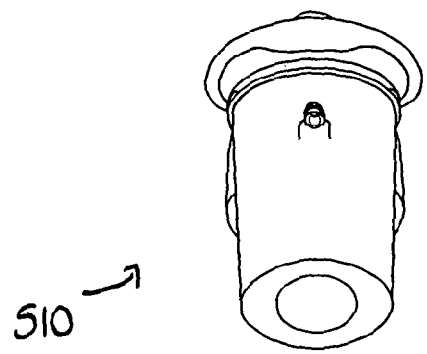
Figure 46:
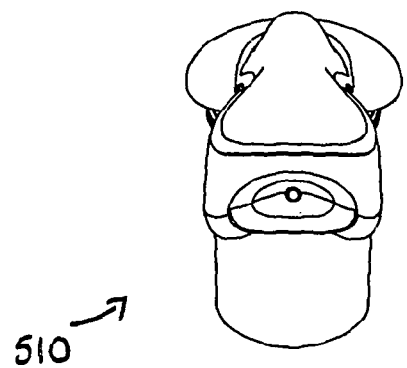
Figure 47:
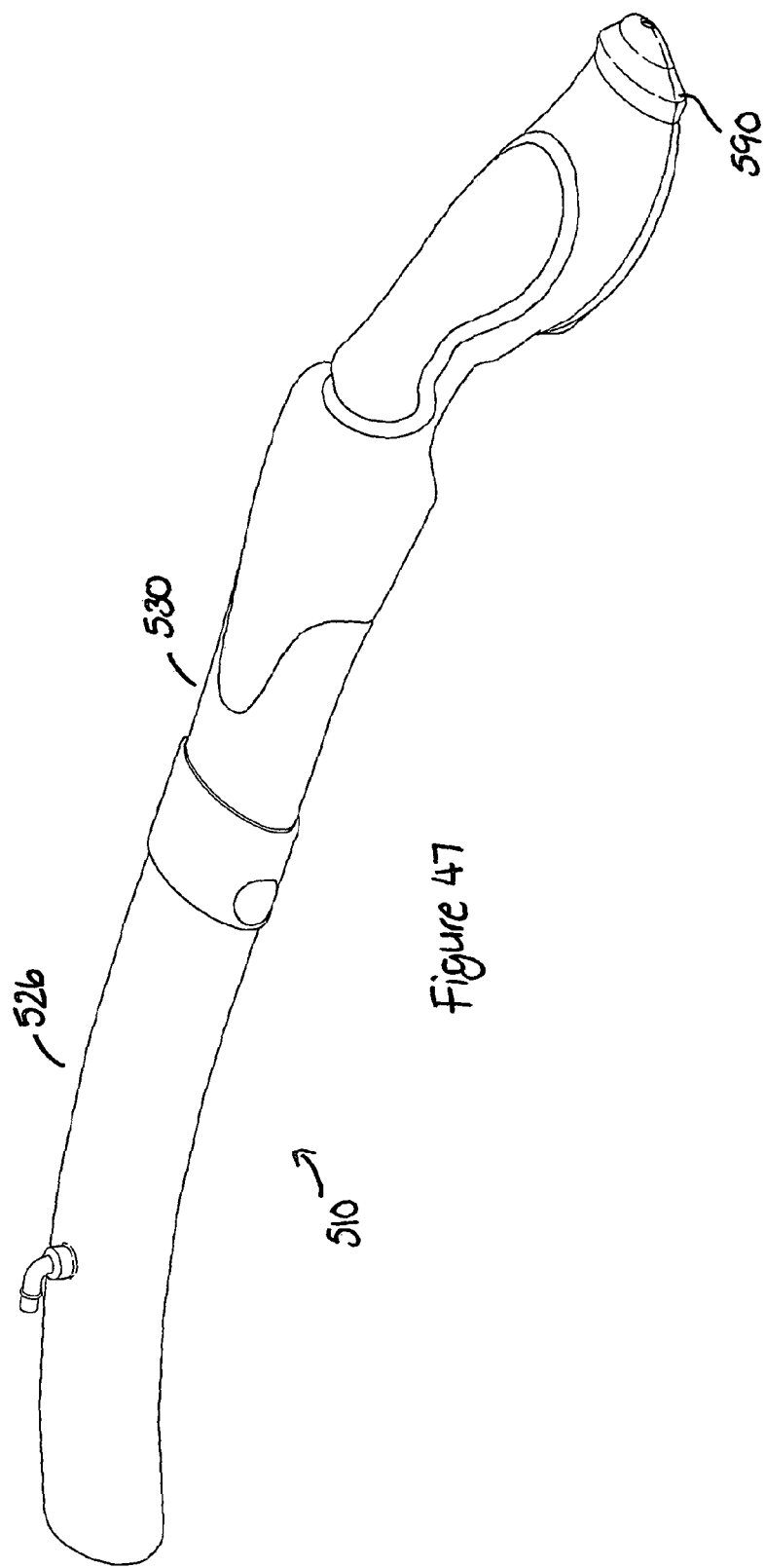
Figure 48:
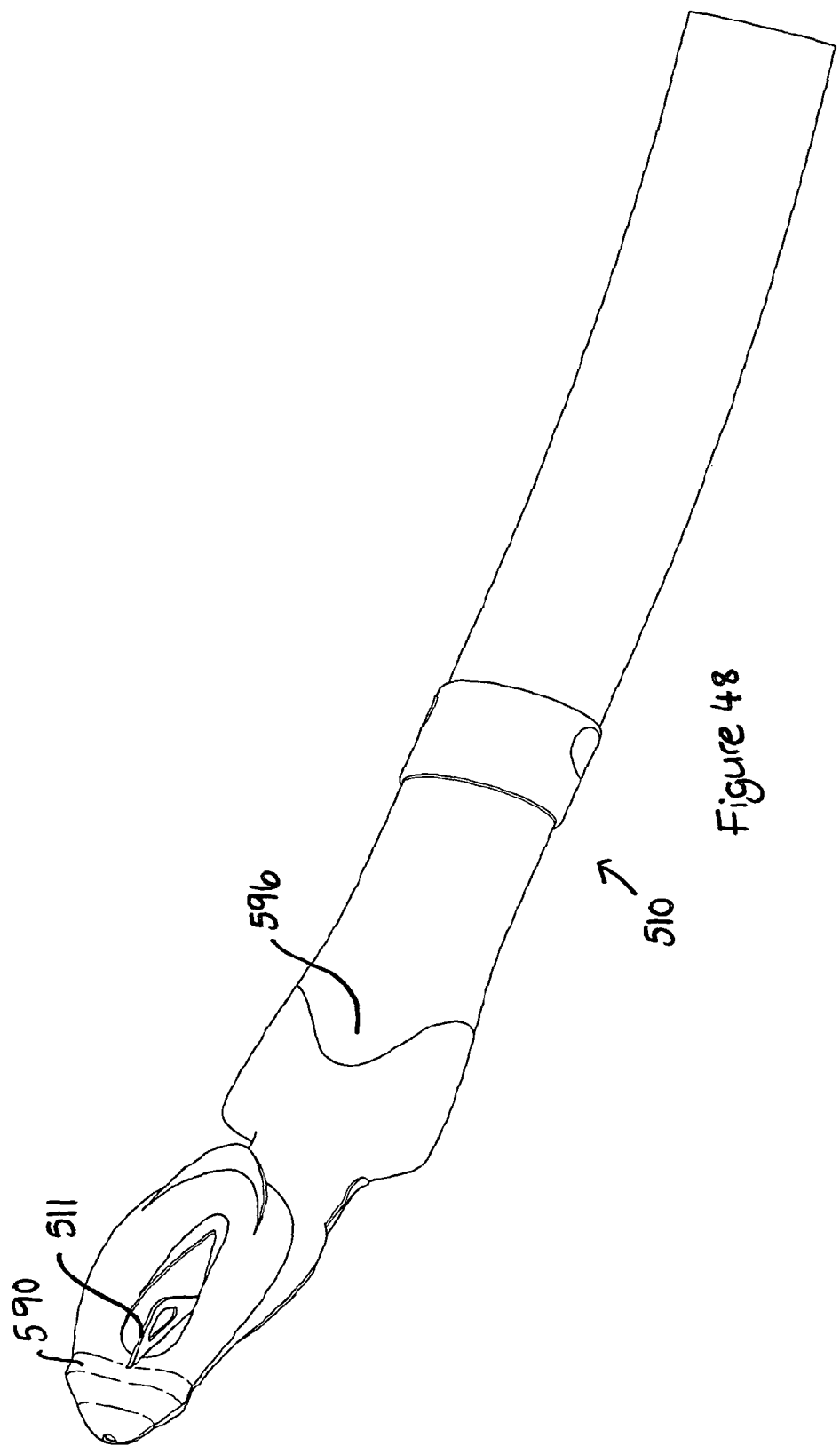

FIGS. 41 to 48 illustrate a sixth an embodiment of the airway device 510. The airway device 510 has an airway tube 512 with a first end 514 and a second end 516. The first end 514 of the airway tube 512 is surrounded by a laryngeal cuff 518. The cuff 518 has a back dorsal portion 520 and a front face portion 522. The front face portion 522 is shaped to form an anatomical fit over the laryngeal inlet of a patient. The second end 516 of the airway tube is fitted with a connector (not shown) such that the second end 516 of the airway tube 512 can be connected to the relevant gas supply. The airway device 510 also has a shoulder 526. The shoulder 526 is used to prevent over-insertion of the airway device 510. The shoulder 526 is located laterally and substantially perpendicular to the direction of the airflow, and thus the airway tube 512. The shoulder 526 is located just above the neck 528 of the airway device 510 where the laryngeal cuff 518 appears to join the airway tube 512 at the second end 514. The shoulder 526 is used to create a point of contact between the airway device 510 and the faucial pillars located at the back of the patient's mouth. This thus creates a positive stopping feature that in use prevents the shoulder portion 526 going forward beyond the faucial pillars of the patient and thus prevents over-insertion of the airway device 510.

The airway device 510 is further provided with a raised portion 538. The raised portion 538 is located on the airway tube 512 above and extending just behind the shoulder 526 towards the second end 516 of the airway tube, when in situ in the horse, the raised portion 538 corresponds to the location of the cavity of the upper mouth arch of the patient called the palatoglossal arch. The raised portion 538 aids in preventing over-insertion of the airway device by being adapted to locate in the cavity of the palatoglossal arch due to the contouring of the raised portion and provides resistance on being moved beyond this position. The raised portion 538 is not meant to be in constant contact with the palatoglossal arch but simply to locate into this cavity to prevent over-insertion and resist movement of the device when in situ.

In order to further discourage over-insertion, the tip 532 of the laryngeal cuff 518 is angled upwards away from the horizontal plane of the laryngeal cuff 518. The tip 532 may be angled from 5° to 80°. The angle of the tip 532 has the effect of increasing the surface area of the tip 532. The tip 532 engages to seal with the top of the oesophagus of the patient when the airway device 510 is correctly inserted. The larger tip 532 surface area creates some resistance with the top of the oesophagus during insertion which would be felt by the clinician during insertion to determine that the airway 510 device has been correctly inserted. The tip is formed from materials of two different hardnesses. A soft material is used for the front face portion of the tip 534 and a harder material is used for the rear dorsal portion of the tip 536. This results in a tip which has strength to prevent the tip folding over on itself and soft to prevent damage to the oesophagus upon contact.

The tip 532 of the laryngeal cuff 518 is also provided with an annular sealing bulge 590. The annular sealing bulge 590 is provided for improved sealing of the tip 532 of the laryngeal cuff 518 in the upper oesophagus region of the patient. The annular sealing bulge is formed of a soft polymeric or other plastics material with a shore hardness of between 40 and 000 on the A scale. The annular sealing bulge 590 allows for better sealing with a more variable range of upper oesophageal features.

The airway device 510 is also provided with a concave portion or scallop 596 on the airway tube 512. The concave portion or scallop 596 is located on the opposite side of the airway tube 512 to the raised portion 538 around the location of the shoulder 526. The concave portion of scallop 596 is located at the back of the tongue of the patient in use. The concave portion or scallop 596 acts to reduce the amount of pressure being applied to the convex portion of back of the tongue. When pressure is applied to the convex portion at the back of the tongue, this results in the formation of blue tongue in patients because the pressure to the tongue constricts blood vessels.

In addition the airway device 510 is further provided with an inflatable back and neck cuff 525 and inflation line (not shown) to inflate the inflatable back and neck cuff 525. The inflatable back and neck cuff 525 is designed to lay flush with profile of the back dorsal portion 520 of the laryngeal cuff 518 when not inflated, and this does not interfere with the insertion of the device 510. The inflatable back and neck cuff 525 is provided to give flexibility of fit of the device in different patients. The inflatable back and neck cuff 525 when inflated is adapted to expand to fit into the large void area in horses for example which would otherwise lead to a reduced seal of the laryngeal cuff around the laryngeal inlet of the patient.

Furthermore the distal opening of the cuff 518 is provided with a bracket 511 to provide strength to the tip 532 of the device 510 and to prevent downfolding of the horse epiglottis into the opening of the cuff and blocking the air flow.

The airway tube 512 is designed in two portions 529 and 530 such that the device 510 can be split into two portions to fit into standard sized autoclaves for sterilization between uses.

The invention claimed is:

1. An airway device for human or animal use, the airway device including an airway tube having a first open end and a second open end, wherein the first open end of the airway tube is surrounded by a laryngeal cuff formed of a polymeric or other plastic material, wherein the laryngeal cuff includes a back dorsal portion, a front face portion and a tip, the tip including a front face portion and a dorsal portion, wherein the front face portion of the laryngeal cuff has a shape adapted to form an anatomical fit over the laryngeal inlet of a human or animal patient, and form a seal with the laryngeal inlet of the patient, wherein the tip includes an unsymmetrical annular sealing bulge formed at least in part from a soft polymeric or other plastics material with a Shore hardness of between 40 and 000 on the A scale, wherein the unsymmetrical annular sealing bulge is larger on the front face portion of the tip than on the dorsal portion of the tip whereby to form a better seal with the laryngeal inlet of the patient, and wherein the unsymmetrical annular sealing bulge is configured to wedge into an upper esophagus region of the human or animal patient.

2. An airway device as claimed in claim 1 wherein the unsymmetrical annular sealing bulge is provided for improved sealing of the tip of the laryngeal cuff in the upper esophagus region of the human or animal patient.

3. An airway device as claimed in claim 1 wherein the unsymmetrical annular sealing bulge is provided with a contoured surface.

4. An airway device as claimed in claim 3 wherein the contoured surface reduces the surface areas of the unsymmetrical annular sealing bulge that is in contact with the upper esophagus region of the patient when in situ in the patient to reduce trauma resulting from contact between the bulge and such features whilst still creating a good seal therewith.

5. An airway device as claimed in claim 3 wherein the contoured surface is a dimpled surface.

6. An airway device as claimed in claim 3 wherein the contoured surface is a pimpled surface.

7. An airway device as claimed in claim 3 wherein the contoured surface is provided with a series of ridges.

8. An airway device as claimed in claim 3 wherein the contoured surface is provided with a series of indentations.

9. An airway device as claimed in claim 3 wherein the contoured surface is provided with a series of valleys.

10. An airway device as claimed in claim 3 wherein the contoured surface is provided with a series of protrusions.

11. An airway device as claimed in claim 1 wherein the unsymmetrical annular sealing bulge on the front face portion of the tip is provided with a inner core formed from a rigid material covered or coated with a soft polymeric or other plastic material with a Shore hardness of between 40 and 000 on the A scale.

12. An airway device as claimed in claim 1, wherein the unsymmetrical annular sealing bulge surrounds the tip, at least in part, and extends from the front face portion and the dorsal portion of the tip.

* * * * *